United States Patent
Shirota et al.

(10) Patent No.: US 11,021,436 B2
(45) Date of Patent: Jun. 1, 2021

(54) COMPOUND, LIQUID COMPOSITION, THERMAL TRANSFER RECORDING SHEET, TONER, RESIST COMPOSITION FOR COLOR FILTER, AND COLOR FILTER

(71) Applicant: CANON KABUSHIKI KAISHA, Tokyo (JP)

(72) Inventors: Koromo Shirota, Kawasaki (JP); Taichi Shintou, Saitama (JP); Ai Hayakawa, Ashigarakami-gun (JP); Tsuyoshi Santo, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/930,463

(22) Filed: Jul. 16, 2020

(65) Prior Publication Data

US 2020/0347007 A1 Nov. 5, 2020

Related U.S. Application Data

(63) Continuation of application No. PCT/JP2019/001367, filed on Jan. 18, 2019.

(30) Foreign Application Priority Data

Jan. 25, 2018 (JP) .............................. JP2018-010392

(51) Int. Cl.
*C07C 211/64* (2006.01)
*B41M 5/385* (2006.01)
(Continued)

(52) U.S. Cl.
CPC ......... *C07C 211/64* (2013.01); *B41M 5/3854* (2013.01); *B41M 5/39* (2013.01);
(Continued)

(58) Field of Classification Search
None
See application file for complete search history.

(56) References Cited

U.S. PATENT DOCUMENTS 3,251,881 A 5/1966 Susi et al.
3,484,467 A 12/1969 Susi et al.
(Continued)

FOREIGN PATENT DOCUMENTS

DE 4217973 A1 12/1993
JP 61-69991 A 4/1986
(Continued)

OTHER PUBLICATIONS

Grossmann ("Electron Delocalization in One-Electron Oxidized Aniline Oligomers, Paradigms for Polyaniline. A Study by Paramagnetic Resonance in Fluid Solution" J. Phys. Chem. B 2004, 108, p. 4669-4672) (Year: 2004).*

(Continued)

*Primary Examiner* — Amy C Bonaparte
(74) *Attorney, Agent, or Firm* — Venable LLP

(57) ABSTRACT

Provided is, for example, a compound excellent in light fastness and storage stability. The compound is characterized by having a structure represented by the following formula (1) or (2).

(Continued)

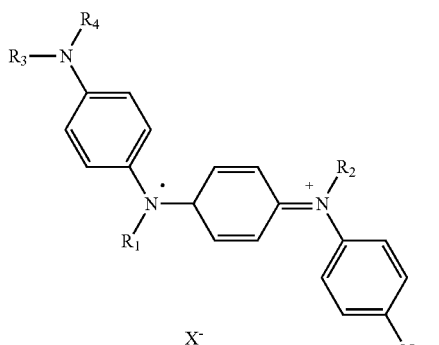

Formula (1)

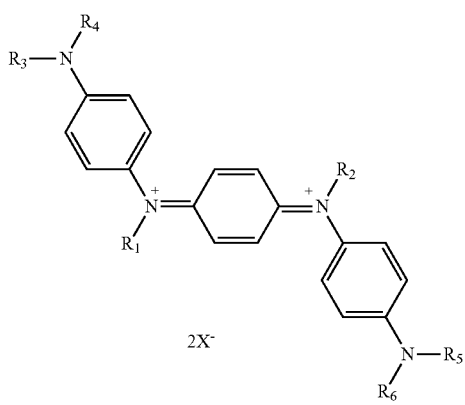

Formula (2)

9 Claims, 2 Drawing Sheets

(51) Int. Cl.
*B41M 5/39* (2006.01)
*B41M 5/395* (2006.01)
*G02B 5/20* (2006.01)
*C07C 251/30* (2006.01)
*G02B 5/22* (2006.01)

(52) U.S. Cl.
CPC ........... *B41M 5/395* (2013.01); *C07C 251/30* (2013.01); *G02B 5/20* (2013.01); *G02B 5/223* (2013.01)

(56) References Cited

U.S. PATENT DOCUMENTS

| | | |
|---|---|---|
| 2019/0217648 A1 | 7/2019 | Katsumoto et al. |
| 2020/0339814 A1 | 10/2020 | Shintou et al. |

FOREIGN PATENT DOCUMENTS

| | | | |
|---|---|---|---|
| JP | S6191914 | * | 5/1986 |
| JP | S6232132 | * | 5/1986 |
| JP | 62-32132 A | | 2/1987 |
| JP | 3-224793 A | | 10/1991 |
| JP | H03224793 | * | 10/1991 |
| JP | 11-105423 A | | 4/1999 |
| JP | 2001-138623 A | | 5/2001 |
| JP | 2001138623 | * | 5/2001 |
| JP | 2001-158879 A | | 6/2001 |
| JP | 2001158879 | * | 6/2001 |
| JP | 2006-137933 A | | 6/2006 |
| JP | 2006137933 | * | 6/2006 |
| JP | 2012-250400 A | | 12/2012 |
| WO | 2019/146506 A1 | | 8/2019 |

OTHER PUBLICATIONS

Honzl ("Organic Semiconductors: donor-acceptor complexes of conjugated bases with a repeating structural unit" Journal of Polymer Science, 1969, p. 4465-4481). (Year: 1969).*

Khalid ("Polyaniline: Synthesis Methods, Doping and Conduction Mechanism", DOI: http://dx.doi.org/10.5772/intechopen.79089, 2018, p. 1-17-see whole document, particularly section 3 on p. 5-12) (Year: 2018).*

T. Moll et al., "Electrochemical and Spectroscopic Properties of Oligoanilines," 55-57 (2-3) Synthetic Met. 1521-1526 (1993).

International Search Report in International Application No. PCT/JP2019/001367 (dated Apr. 2019).

International Preliminary Report on Patentability in International Application No. PCT/JP2019/001367 (dated Jul. 2020).

* cited by examiner

COMPOUND, LIQUID COMPOSITION, THERMAL TRANSFER RECORDING SHEET, TONER, RESIST COMPOSITION FOR COLOR FILTER, AND COLOR FILTER

CROSS-REFERENCE TO RELATED APPLICATIONS

This application is a Continuation of International Patent Application No. PCT/JP2019/001367, filed Jan. 18, 2019, which claims the benefit of Japanese Patent Application No. 2018-010392 filed Jan. 25, 2018, both of which are hereby incorporated by reference herein in their entirety.

BACKGROUND OF THE INVENTION

Field of the Invention

The present disclosure relates to a compound, a liquid composition, a thermal transfer recording sheet, a toner, a resist composition for a color filter, and a color filter.

Description of the Related Art

In recent years, along with the spread of a portable color display device, there has been a rapidly growing demand for easy color printing of a photograph taken with such device, a photograph processed therewith, and a document produced therewith.

An electrophotographic system, an inkjet system, a thermal transfer recording system, or the like has been known as a color print system. Of those, the thermal transfer recording system is excellent as a method by which such photograph or document as described above can be easily printed irrespective of its surrounding environment because the system enables the printing by a dry process, and can downsize an apparatus for the printing and is hence excellent in portability of a printer. Of the thermal transfer recording systems, a thermal sublimation transfer system involves: transferring and diffusing a dye as a single molecule onto an image receiving sheet with thermal energy; and fixing the dye to form an image. In recent years, the thermal sublimation transfer system has been attracting attention again because the system can represent a color tone and gradation close to those of a silver-halide photo. However, the system has involved a problem in terms of light fastness because the dye diffuses as a single molecule in a substrate.

In Japanese Patent Application Laid-Open No. 2001-158879, there is a disclosure of a thermal transfer sheet that contains a fading inhibitor and hence can improve the light fastness of a coloring material after thermal transfer. In addition, in Japanese Patent Application Laid-Open No. 2012-250400, as a protective layer transfer sheet that can impart high light fastness to an image formed on a transfer target material, there is a disclosure of a protective layer transfer sheet containing, in its surface layer, a copolymer obtained by copolymerizing at least styrene and a UV-absorbing monomer.

In addition, in recent years, along with the advance of various technologies, to represent a wider color gamut in products ranging from a color display to a printed product, an investigation on the use of a high-chroma dye in a field where a pigment has heretofore been used has been advanced.

In the field of a color display, heretofore, a pigment has generally been used as a colorant in a color filter for a color display using a liquid crystal. However, the color filter using the pigment has involved many problems, such as a depolarization action (the breakage of polarization), a reduction in contrast ratio of the color display of a liquid crystal display, a reduction in brightness of the color filter, and a reduction in dispersion stability of the pigment against an organic solvent or a polymer. In view of the foregoing, a color filter using a dye as a colorant has been attracting attention.

Also in the field of a color toner to be used in the electrophotographic system, to improve color developability, there has been reported an example in which a dye is used as a colorant instead of a pigment that has heretofore been used. In German Patent Application Laid-Open No. 4,217,973, there is a disclosure of an example in which an azomethine-based dye is used as a colorant for a toner.

In each of the color display and the toner, however, the high-chroma dye has light fastness lower than that of a related-art pigment, and hence has involved a problem in that the storage stability of a colored product is poor. Accordingly, measures to achieve both of light fastness and high chroma have been required.

An object of the present disclosure is to provide a compound that improves the light fastness of a colored product. Another object of the present disclosure is to provide a liquid composition including the compound. Still another object of the present disclosure is to provide a thermal transfer recording sheet, a toner, and a resist composition for a color filter each of which is excellent in light fastness through use of the compound.

SUMMARY OF THE INVENTION

At least one embodiment of the present disclosure, there is provided a compound, which is represented by the following formula (1) or (2).

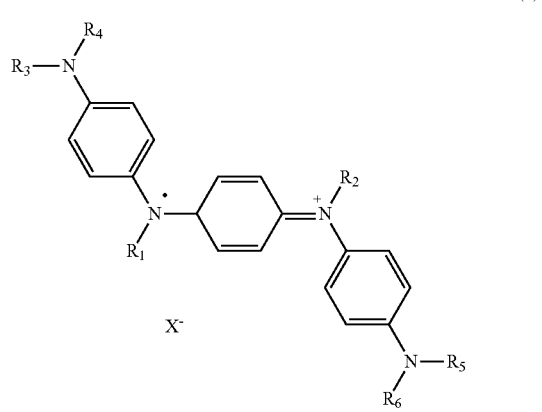

Formula (1)

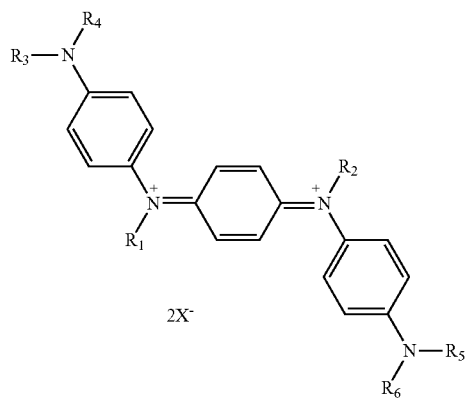

Formula (2)

In the formula (1) and the formula (2), $R_1$ and $R_2$ each independently represent an unsubstituted alkyl group having 1 to 8 carbon atoms, $R_3$ and $R_4$ each independently represent a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_3$ and $R_4$ are bonded to each other to form a nitrogen-containing heterocycle, $R_5$ and $R_6$ each independently represent a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_5$ and $R_6$ are bonded to each other to form a nitrogen-containing heterocycle, a substituent in the substituted alkyl group represented by any one of $R_3$ to $R_6$ is a cyano group or an alkoxy group, provided that a number of carbon atoms of the substituent is excluded from the number of carbon atoms specified above, a substituent in each of the substituted alkenyl group, the substituted aralkyl group, and the substituted aryl group each represented by any one of $R_3$ to $R_6$ is a functional group selected from the group consisting of an alkyl group, a cyano group, and an alkoxy group, provided that a number of carbon atoms of the substituent is excluded from the number of carbon atoms specified above, and $X^-$ represents an anion.

In addition, according to at least one embodiment of the present disclosure, there is provided a liquid composition including: a medium; and a compound and a coloring material present under a state of being dissolved or dispersed in the medium, wherein the compound is the above-mentioned compound.

In addition, according to at least one embodiment of the present disclosure, there is provided a thermal transfer recording sheet including: a substrate; and a coloring material layer formed on the substrate, wherein the coloring material layer contains the above-mentioned compound.

In addition, according to at least one embodiment of the present disclosure, there is provided a thermal transfer recording sheet including: a substrate; and a coloring material layer and a protective layer formed on the substrate, the coloring material layer and the protective layer being formed field sequentially, wherein the protective layer contains the above-mentioned compound.

In addition, according to at least one embodiment of the present disclosure, there is provided a toner or a resist composition for a color filter including: a binder resin; a colorant; and the above-mentioned compound.

Further, according to at least one embodiment of the present disclosure, there is provided a color filter including a resist layer containing the above-mentioned compound.

Further features of the present invention will become apparent from the following description of exemplary embodiments with reference to the attached drawings.

DESCRIPTION OF THE EMBODIMENTS

Figure 1:
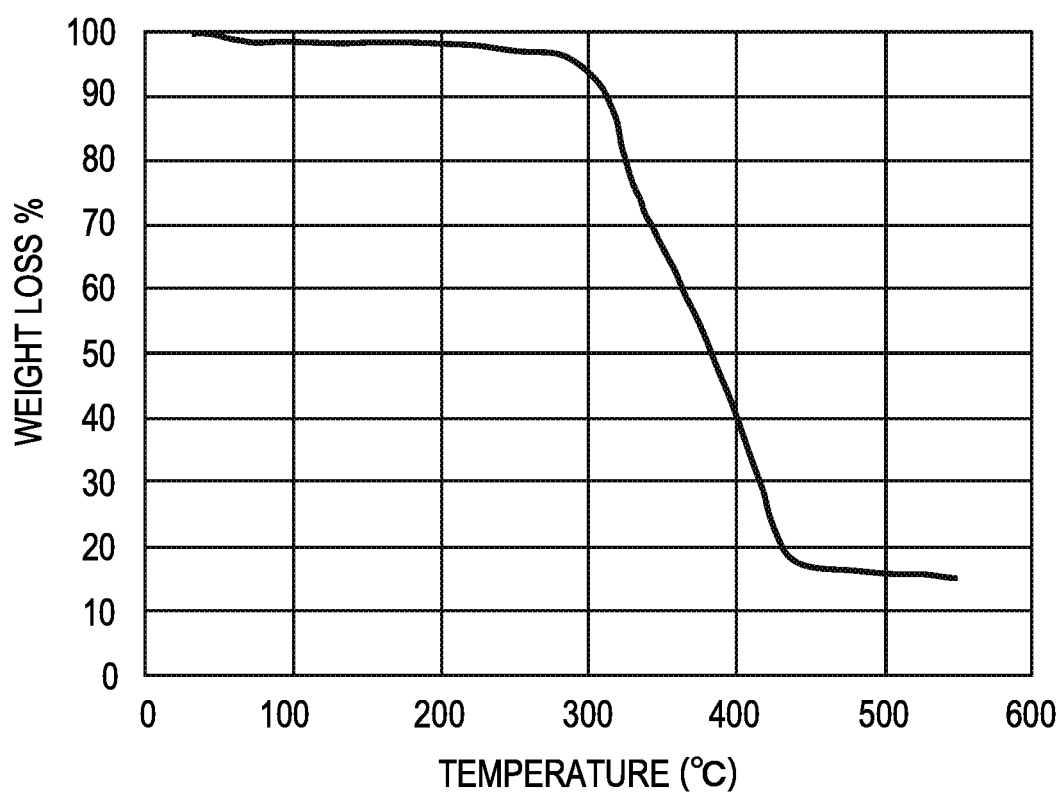
FIG. 1 is a thermogravimetric-differential thermal analysis (TG-DTA) graph of a compound (1-3) according to at least one embodiment of the present disclosure, the graph being obtained by increasing the temperature of 5.6 mg of the sample from 45° C. to 550° C. at 10° C./min under a nitrogen environment, and measuring the weight loss of the sample.

Embodiments of the present disclosure are described in detail below. However, the present disclosure is not limited to the embodiments.

The inventors have made extensive investigations with a view to solving the above-mentioned problems, and as a result, have found that the use of a compound represented by the formula (1) or (2) according to at least one embodiment of the present disclosure improves the light fastness of a colored product.

Formula (1)

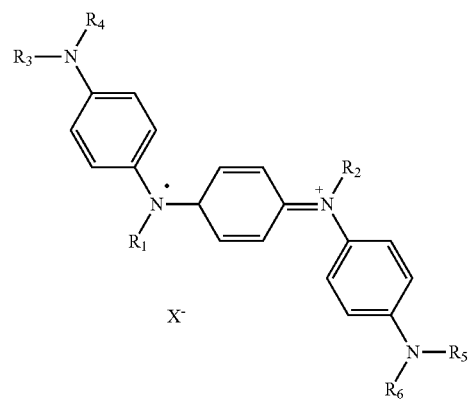

Formula (2)

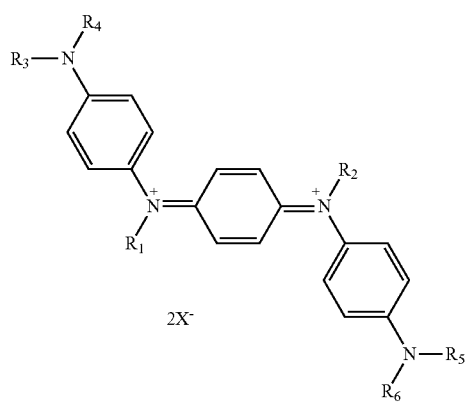

2X⁻

Related-art compound (1)

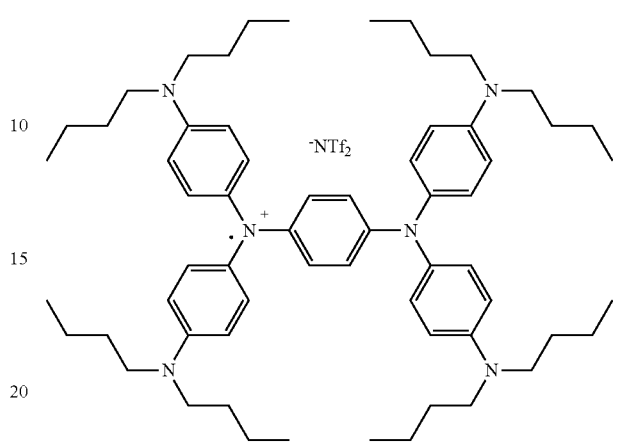

In the formula (1) and the formula (2), $R_1$ and $R_2$ each independently represent an unsubstituted alkyl group having 1 to 8 carbon atoms, $R_3$ and $R_4$ each independently represent a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_3$ and $R_4$ are bonded to each other to form a nitrogen-containing heterocycle, $R_5$ and $R_6$ each independently represent a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_5$ and $R_6$ are bonded to each other to form a nitrogen-containing heterocycle, a substituent in the substituted alkyl group represented by any one of $R_3$ to $R_6$ is a cyano group or an alkoxy group, provided that the number of carbon atoms of the substituent is excluded from the number of carbon atoms specified above, a substituent in each of the substituted alkenyl group, the substituted aralkyl group, and the substituted aryl group each represented by any one of $R_3$ to $R_6$ is a functional group selected from the group consisting of an alkyl group, a cyano group, and an alkoxy group, provided that the number of carbon atoms of the substituent is excluded from the number of carbon atoms specified above, and $X^-$ represents an anion.

The inventors have considered that the presence of the compound to be added for improving the light fastness in the vicinity of a dye molecule in a recorded product is a necessary condition for solving the above-mentioned problems. Accordingly, such a related-art compound (1) as described in the related art does not have a sufficient light fastness-improving effect because the compound has a large molecular weight, and hence cannot approach the vicinity of the dye molecule in the recorded product. In addition, a liquid composition containing the compound has involved a problem in terms of stability because the compound has low solubility. The inventors have considered that in contrast, the compound according to at least one embodiment of the present disclosure improves the light fastness of the recorded product because the compound has a small molecular weight, and hence can approach the vicinity of the dye molecule in the recorded product; further, the stability of a liquid composition containing the compound is improved because the compound has high solubility.

In addition, the inventors have found that the use of the compound represented by the formula (1) or (2) provides a thermal transfer recording sheet and a toner for obtaining a recorded product excellent in light fastness, and a resist composition for a color filter excellent in light fastness.

First, the compounds represented by the formula (1) and the formula (2) are described.

In the formula (1), the unsubstituted alkyl group having 1 to 8 carbon atoms represented by any one of $R_1$ and $R_2$ is not particularly limited, but examples thereof include the following groups: a methyl group, an ethyl group, a n-propyl group, an iso-propyl group, a n-butyl group, a sec-butyl group, a tert-butyl group, an iso-butyl group, an octyl group, a cyclobutyl group, a cyclopentyl group, a cyclohexyl group, a methylcyclohexyl group, a cyclohexylmethyl group, a 2-ethylpropyl group, and a 2-ethylhexyl group.

A case in which the alkyl group is the alkyl group having 1 to 4 carbon atoms out of those groups is preferred from the viewpoint that a compound that improves the light fastness of a colored product is obtained. In particular, a case in which the alkyl group is a methyl group is more preferred.

In the formula (1), the unsubstituted alkyl group having 1 to 8 carbon atoms represented by any one of $R_3$ and $R_4$ is not particularly limited, but examples thereof include the following groups: a methyl group, an ethyl group, a n-propyl group, an iso-propyl group, a n-butyl group, a sec-butyl group, a tert-butyl group, an iso-butyl group, an octyl group, a cyclobutyl group, a cyclopentyl group, a cyclohexyl group, a methylcyclohexyl group, a cyclohexylmethyl group, a 2-ethylpropyl group, and a 2-ethylhexyl group.

Examples of the substituent of the substituted alkyl group in any one of $R_3$ and $R_4$ may include a cyano group and an alkoxy group.

In the formula (1), the unsubstituted alkenyl group in any one of $R_3$ to $R_6$ is not particularly limited, but examples thereof may include a vinyl group, a propenyl group, a butenyl group, a pentenyl group, a hexenyl group, a heptenyl group, and an octanyl group.

Examples of the substituent of the substituted alkenyl group include an alkyl group, a cyano group, and an alkoxy group.

In the formula (1), the unsubstituted aralkyl group having 7 to 12 carbon atoms in any one of $R_3$ to $R_6$ is not particularly limited, but examples thereof include a benzyl group and a naphthyl group. Examples of the substituent of the substituted aralkyl group may include an alkyl group, a cyano group, and an alkoxy group.

In the formula (1), the unsubstituted aryl group having 6 to 12 carbon atoms in any one of $R_3$ to $R_6$ is not particularly limited, but examples thereof include a phenyl group and a naphthyl group.

Examples of the substituent of the substituted aryl group may include an alkyl group, a cyano group, and an alkoxy group.

$R_3$ and $R_4$, and/or $R_5$ and $R_6$ may be bonded to each other to form a nitrogen-containing heterocycle. That is, a cyclic structure containing $R_3$, $R_4$, and a nitrogen atom (N atom), or a cyclic structure containing $R_5$, $R_6$, and a nitrogen atom (N atom) may be formed. The cyclic structure is not particularly limited, but examples thereof may include: a five-membered ring that may have a substituent; a six-membered ring that may have a substituent; and a seven-membered ring that may have a substituent.

More specific examples of the cyclic structure may include the following structures. That is, the five-membered ring may be, for example, a pyrrolidine ring, examples of the six-membered ring may include a piperidine ring, a morpholine ring, and a piperazine ring, and the seven-membered ring may be, for example, an azepane ring. Further, examples of the substituent that any such cyclic structure may have may include alkyl groups, such as a methyl group and an ethyl group.

$R_3$ to $R_6$ each preferably represent, for example, an ethyl group, a n-butyl group, or a 2-ethylhexyl group from the viewpoint that a compound that improves the light fastness of a colored product is obtained.

In the formulae (1) and the formula (2), the anion that may be represented by $X^-$ is not particularly limited. Examples of the anion include the following anions: a fluorine ion, a chlorine ion, a bromine ion, an iodine ion, a perchlorate ion ($ClO_4^-$), a nitrate ion, a methanesulfonate ion, a benzenesulfonate ion, a p-toluenesulfonate ion, a p-trifluoromethylbenzenesulfonate ion, a 2,3,4,5,6-pentafluorobenzenesulfonate ion, a methylsulfate ion, an ethylsulfate ion, a propylsulfate ion, a tetrafluoroborate ion ($BF_4^-$), a tetraphenylborate ion, a hexafluorophosphate ion ($PF_6^-$), a benzenesulfinate ion, an acetate ion, a trifluoroacetate ion, a propionacetate ion, a benzoate ion, an oxalate ion, a succinate ion, a malonate ion, an oleate ion, a stearate ion, a citrate ion, a picolinate ion, a monohydrogen diphosphate ion, a dihydrogen diphosphate ion, a pentafluoropropionate ion, a pentachlorostannate ion, a chlorosulfonate ion, a fluorosulfonate ion, a trifluoromethanesulfonate ion, a hexafluoroarsenate ion, a hexafluoroantimonate ion ($SbF_6^-$), a molybdate ion, a tungstate ion, a titanate ion, a zirconate ion, a naphthalenedisulfonate ion, a tris(trifluoromethanesulfonyl)methide ion ($C(SO_2CF_3)_3^-$), a bis(trifluoromethanesulfonyl)imide ion ($N(SO_2CF_3)_2^-$), a bis(perfluoroethanesulfonyl)imide ion ($N(SO_2CF_2CF_3)_2^-$), a pentafluorophenylbis(trifluoromethanesulfonyl)methide ion, a tetrakis(pentafluorophenyl)boron ion, and the following anion (1).

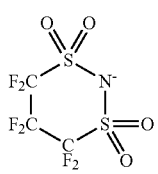

Anion (1)

The following ions are preferred from the viewpoint that a compound that improves the light fastness of a colored product is obtained: a methanesulfonate ion, a trifluoromethanesulfonate ion, a tris(trifluoromethanesulfonyl)methide ion ($C(SO_2CF_3)_3^-$), a bis(trifluoromethanesulfonyl)imide ion ($N(SO_2CF_3)_2^-$), and a bis(perfluoroethanesulfonyl)imide ion ($N(SO_2CF_2CF_3)_2^-$).

Next, a method of producing the compound represented by the formula (1) or (2) according to at least one embodiment of the present disclosure is described. The compound according to at least one embodiment of the present disclosure may be synthesized with reference to a known method described in each of, for example, U.S. Pat. Nos. 3,251,881, 3,484,467, and Japanese Patent Application Laid-Open No. S61-69991. An example of the method of producing the compound represented by the formula (1) that is the compound according to at least one embodiment of the present disclosure is described below, but the production method is not limited thereto.

The presence of structural isomers of the compounds represented by the formula (1) and the formula (2), such as a cis-trans isomer, is conceivable, but such structural isomers fall within the scope of the present disclosure.

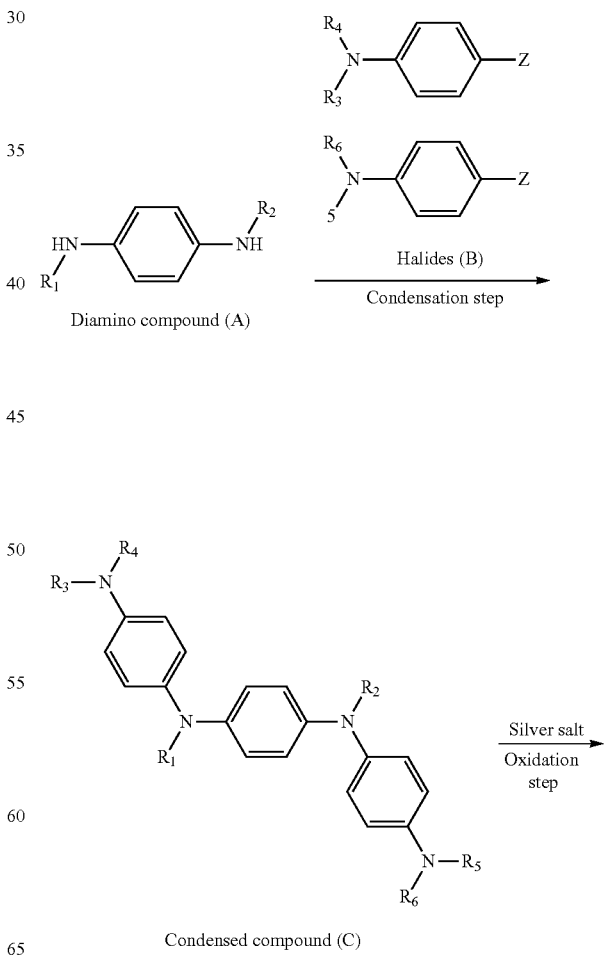

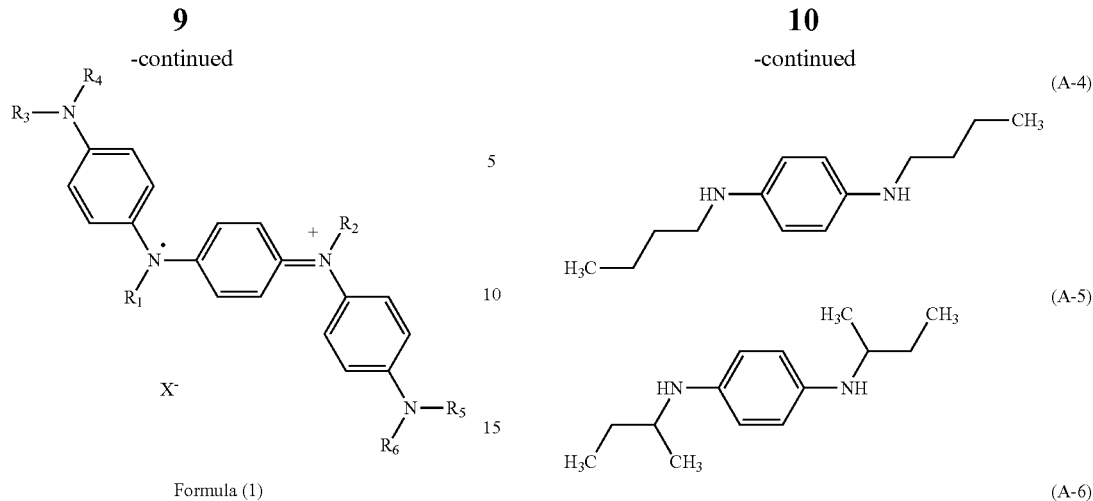

Formula (1)

$R_1$ to $R_6$ in the respective compounds in the reaction formulae are identical in meaning to those described in the foregoing. In addition, isomers of the compound represented by the formula (1) in each of which a cationic species has moved are present, but the isomers each fall within the scope of the present disclosure. The compound represented by the formula (1) may be a mixture of the isomers.

The compound represented by the formula (1) may be produced by, for example, performing a condensation step of condensing the diamino compound (A) and the halides (B) with each other, and then performing an oxidation step based on silver salt oxidation or an electrolytic oxidation reaction.

In addition, when the compound represented by the formula (1) is asymmetric (e.g., when in the formula (1), $R_3$ and $R_4$, and $R_5$ and $R_6$ are different from each other), the compound only needs to be produced by performing condensation reactions with the corresponding halides in a plurality of stages in the condensation step.

[Condensation Step]

The condensation step of obtaining the condensed compound (C), which is an intermediate for obtaining each of the compounds represented by the formula (1) and the formula (2), is described.

The condensed compound (C) may be produced by condensing the diamino compound (A) and the halides (B) with each other.

Preferred examples of the diamino compound (A) are represented by the following formulae (A-1) to (A-11). However, the present disclosure is not limited thereto.

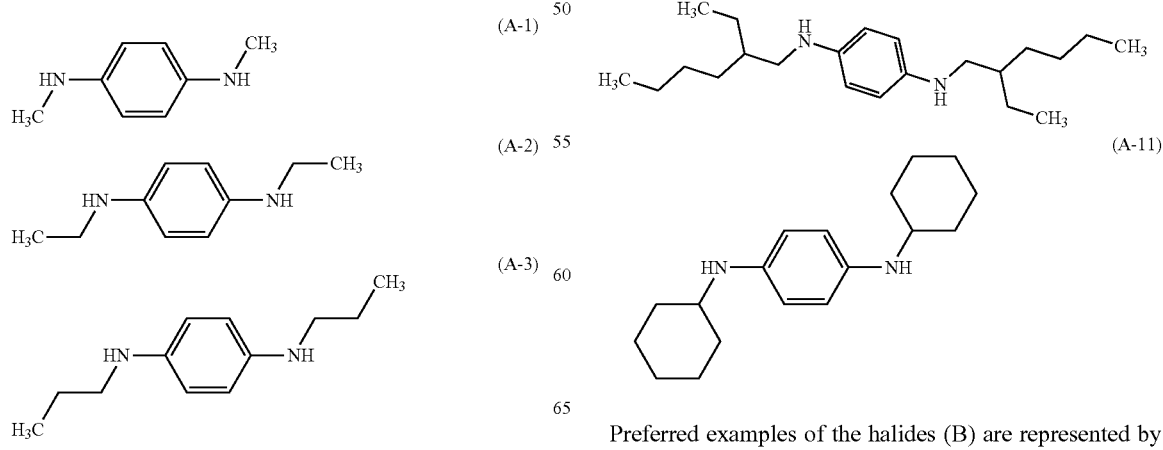

Preferred examples of the halides (B) are represented by the following formulae (B-1) to (B-13). However, the present disclosure is not limited thereto. Although bromo compounds are represented as the halides, chloro compounds and iodine compounds are also permitted.

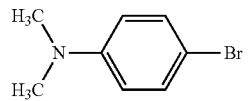
(B-1)

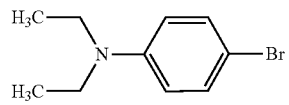
(B-2)

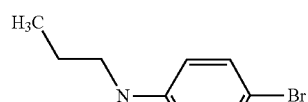
(B-3)

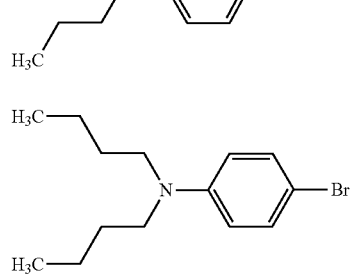
(B-4)

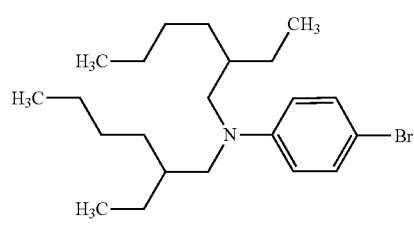
(B-5)

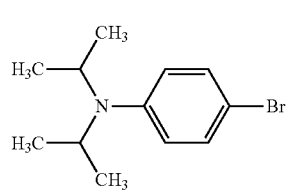
(B-6)

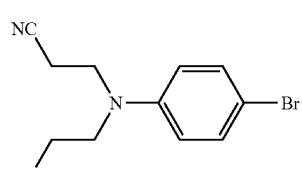
(B-7)

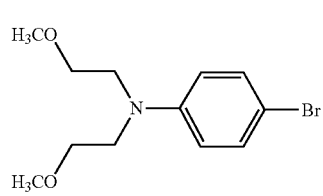
(B-8)

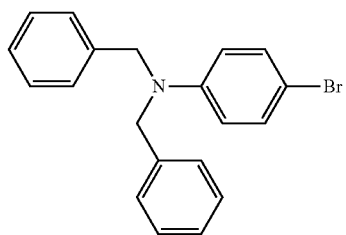
(B-9)

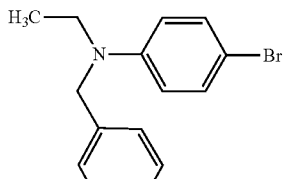
(B-10)

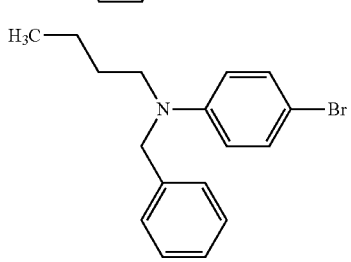
(B-11)

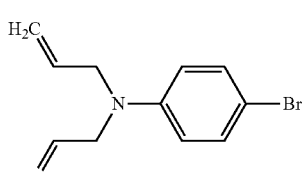
(B-12)

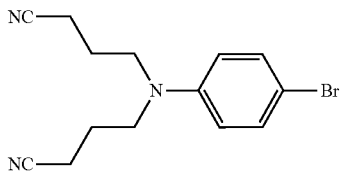
(B-13)

The condensation reaction, which may be performed in the absence of any solvent, is preferably performed in the presence of a solvent. The solvent is not particularly limited as long as the solvent does not inhibit the reaction, and for example, the following solvents may be used alone or in combination thereof in accordance with the solubility of a substrate: methanol, ethanol, n-propanol, isopropanol, n-butanol, toluene, xylene, ethylene glycol, N-methylpyrrolidone, N,N-dimethylacetamide, N,N-dimethylformamide, dimethyl sulfoxide, sulfolane, chlorobenzene, dichlorobenzene, trichlorobenzene, and nitrobenzene.

The step is typically performed at a temperature in the range of from 0° C. to 220° C., and is typically completed within 24 hours.

A case in which the reaction temperature in the condensation step falls within the range of from 5° C. to 180° C. is preferred, and the temperature is more preferably from 10° C. to 120° C. A temperature of less than 0° C. is not preferred because the progress of the reaction becomes remarkably slow. In addition, a temperature of more than 220° C. is not preferred because the decomposition of the compound may occur.

The usage amount of the reaction solvent is preferably from 0.1 mass % to 1,000 mass %, more preferably from 1.0 mass % to 150 mass % with respect to the diamino compound (A).

A condensing agent to be used in the step is not particularly limited, and the reaction is, for example, an Ullmann condensation reaction involving using a copper compound, or a Buchwald-Hartwig reaction involving using a palladium compound.

The usage amount of the condensing agent is preferably from 0.0005 mol to 0.1 mol, more preferably from 0.001 mol to 0.05 mol with respect to 1 mol of the diamino compound (A).

To accelerate the reaction, a co-catalyst for the condensing agent may be used in the step.

A co-catalyst for the Ullmann condensation reaction is not particularly limited as long as the co-catalyst is a known co-catalyst classified as a co-catalyst for the Ullmann condensation reaction. For example, an amine compound, such as 2,2'-bipyridyl or 1,10-phenanthroline, is preferred because the compound is inexpensive and easy to utilize.

Meanwhile, a co-catalyst for the Buchwald-Hartwig reaction is not particularly limited as long as the co-catalyst is a known co-catalyst classified as a co-catalyst for the Buchwald-Hartwig reaction. For example, a phosphorus compound, such as 2-(di-tert-dibutylphosphino)biphenyl, is preferred.

In addition, in the condensation reaction, a base is preferably used for accelerating the reaction. Specific examples of the base include: organic bases, such as pyridine, 2-methylpyridine, piperidine, diethylamine, diisopropylamine, triethylamine, phenylethylamine, isopropylethylamine, methylaniline, 1,4-diazabicyclo[2.2.2]octane (DABCO), tetrabutylammonium hydroxide, and 1,8-diazabicyclo[5.4.0]undecene (DBU); organic metals, such as n-butyllithium and tert-butylmagnesium chloride; inorganic bases, such as sodium borohydride, metallic sodium, potassium hydride, calcium oxide, and potassium carbonate; and metal alkoxides, such as potassium tert-butoxide, sodium tert-butoxide, and sodium ethoxide.

Of those, metal alkoxides, such as potassium carbonate, potassium tert-butoxide, sodium tert-butoxide, and sodium ethoxide, are preferred. In particular, potassium tert-butoxide and sodium tert-butoxide are more preferred. The usage amount of the base is preferably from 0.1 mass % to 20 mass %, more preferably from 0.2 mass % to 5 mass % with respect to the diamino compound (A). In addition, as in the base, a weakly basic salt, such as potassium acetate, may be used.

After the completion of the condensation reaction, a posttreatment is performed in accordance with a posttreatment method typically used in an organic synthesis reaction, and purification, such as a liquid-separating operation, recrystallization, reprecipitation, or column chromatography, is performed as required. Thus, the compound according to at least one embodiment of the present disclosure represented by the condensation compound (C) can be obtained with high purity.

[Oxidation Step]

The compound represented by the formula (1) or (2) may be produced by subjecting the condensed compound (C) obtained in the condensation step to silver salt oxidation or an electrolytic oxidation reaction. When 1-fold mol of the silver salt is used with respect to 1 mol of the condensed compound (C) in the oxidation step, the compound represented by the formula (1) is produced. In addition, when 2-fold mol of the silver salt is used with respect to 1 mol of the condensed compound (C), the compound represented by the formula (2) is produced.

Preferred compound examples of the compound according to at least one embodiment of the present disclosure represented by the formula (1) are represented by the following compounds (1-1) to (1-15). However, the present disclosure is not limited thereto. Tf represents a trifluoromethanesulfonyl group ($CF_3SO_2$—).

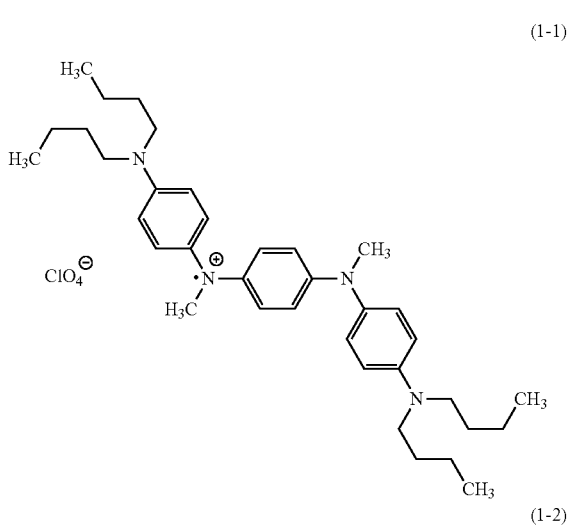

(1-1)

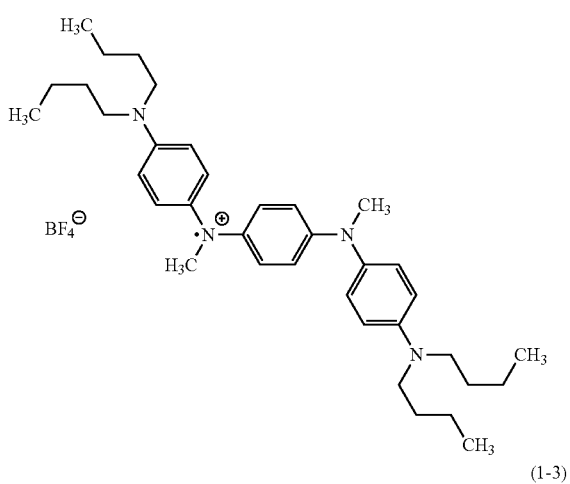

(1-2)

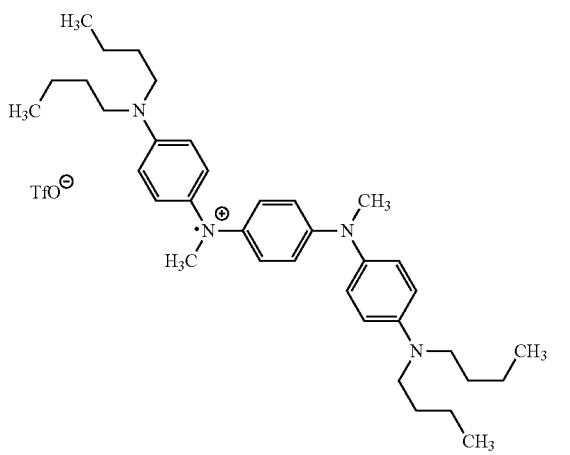

(1-3)

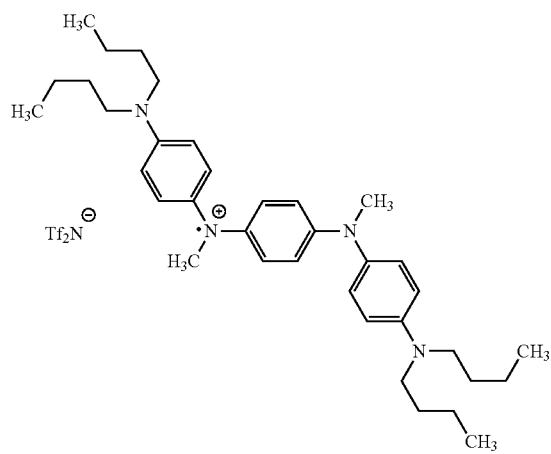
(1-4)
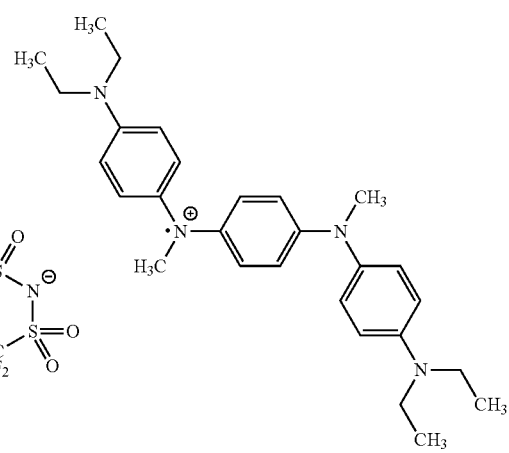
(1-7)
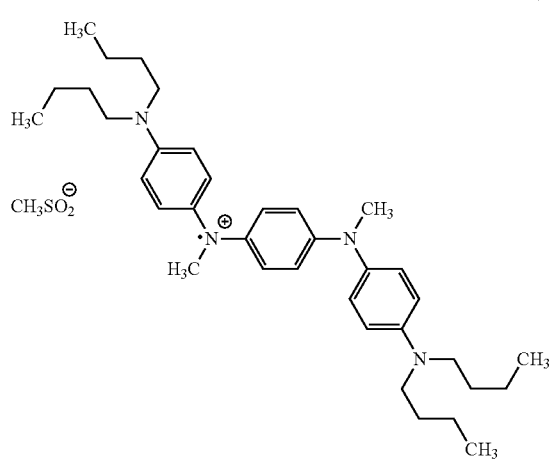
(1-5)
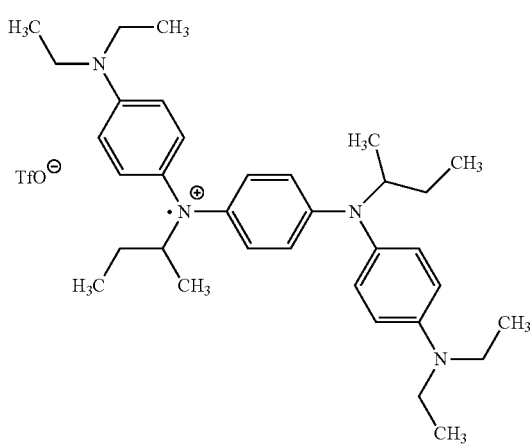
(1-8)
(1-6)
(1-9)

(1-10)
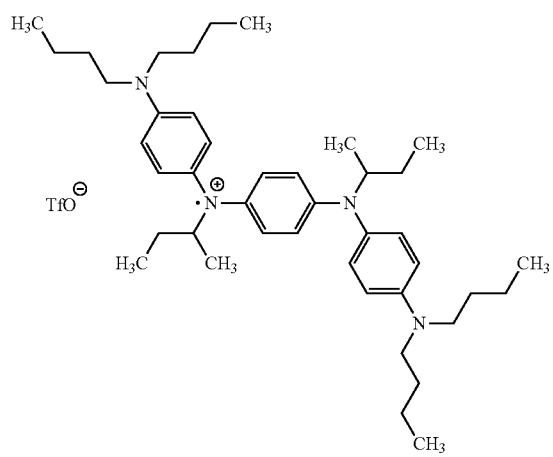
(1-11)
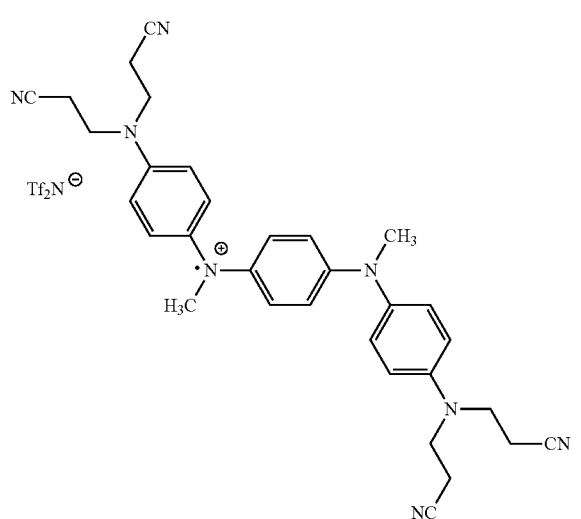
(1-12)
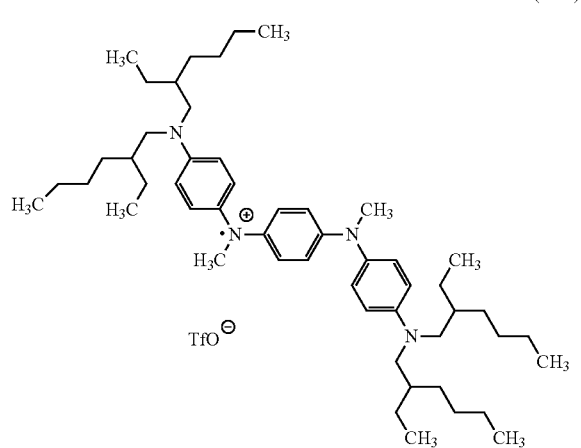
(1-13)
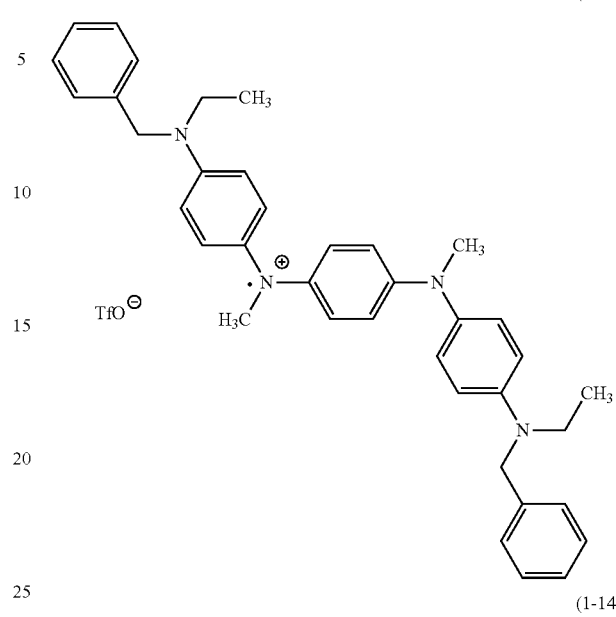
(1-14)
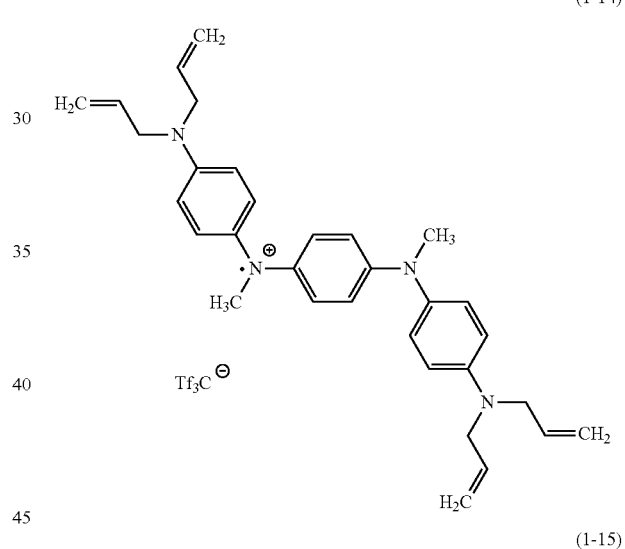
(1-15)
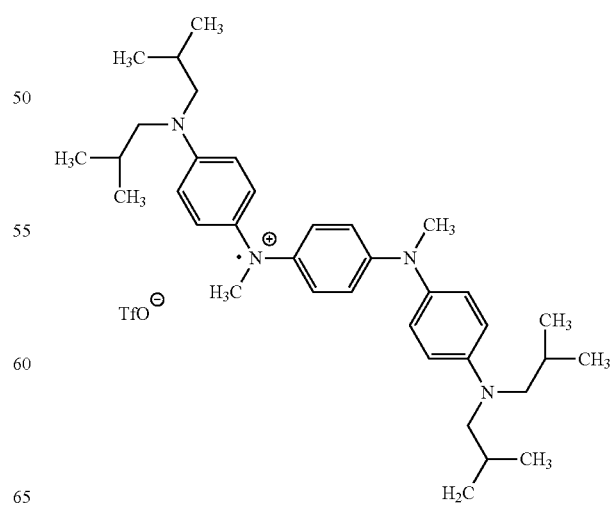

At least one kind of the compound (1-3), (1-4), (1-5), (1-6), (1-8), (1-10), or (1-12) is preferably used from the viewpoint of improving the light fastness of a colored product. At least one kind of the compound (1-3), (1-8), or (1-12) is particularly preferably used.

In addition, preferred compound examples of the compound according to at least one embodiment of the present disclosure represented by the formula (2) are represented by the following compounds (2-1) to (2-15). However, the present disclosure is not limited thereto. Tf represents a trifluoromethanesulfonyl group.

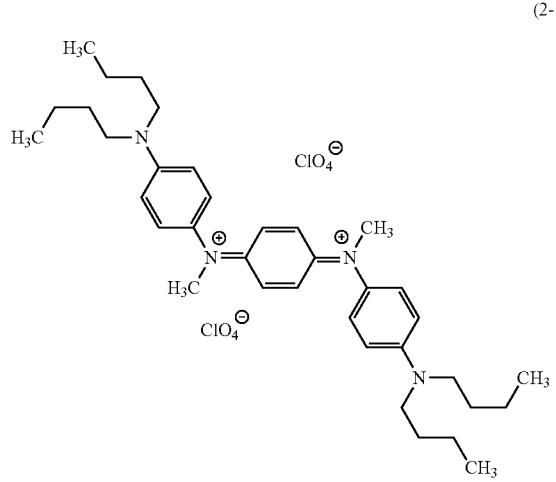
(2-1)

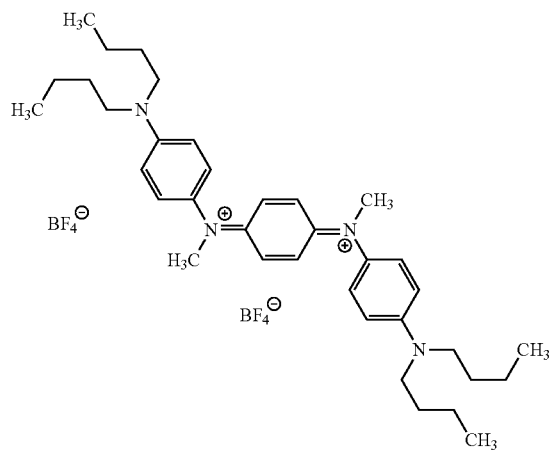
(2-2)

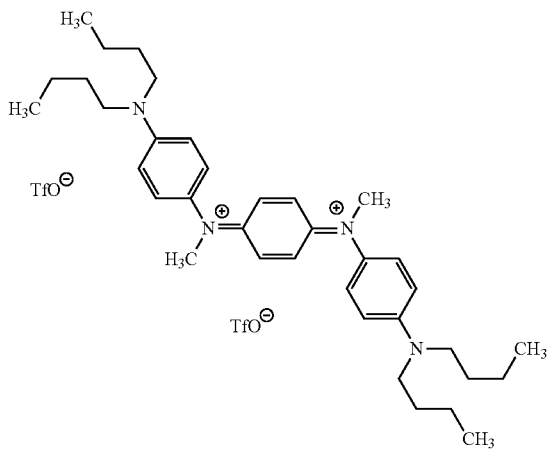
(2-3)

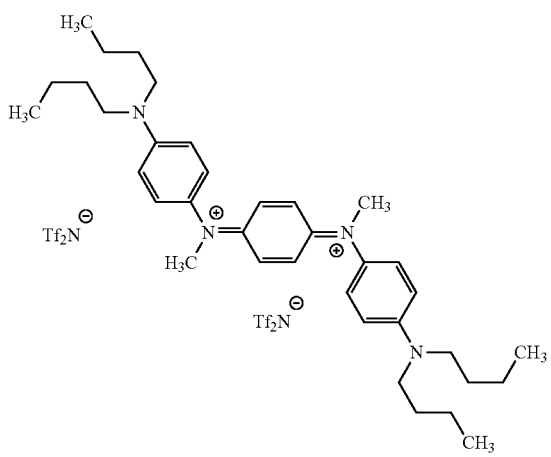
(2-4)

(2-5)

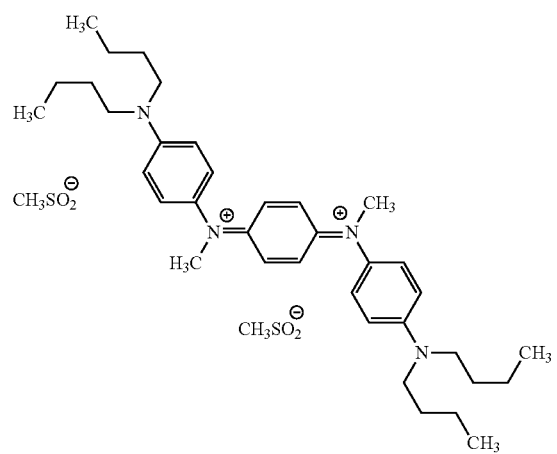
(2-6)
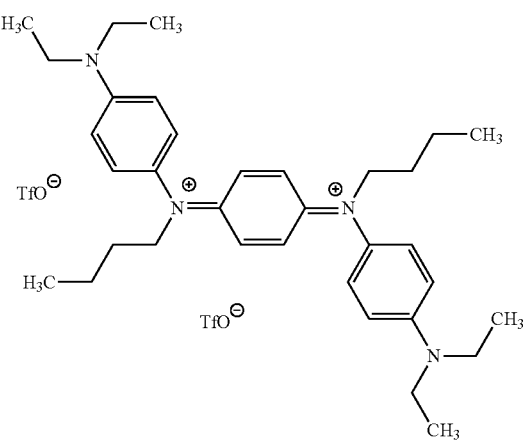
(2-9)
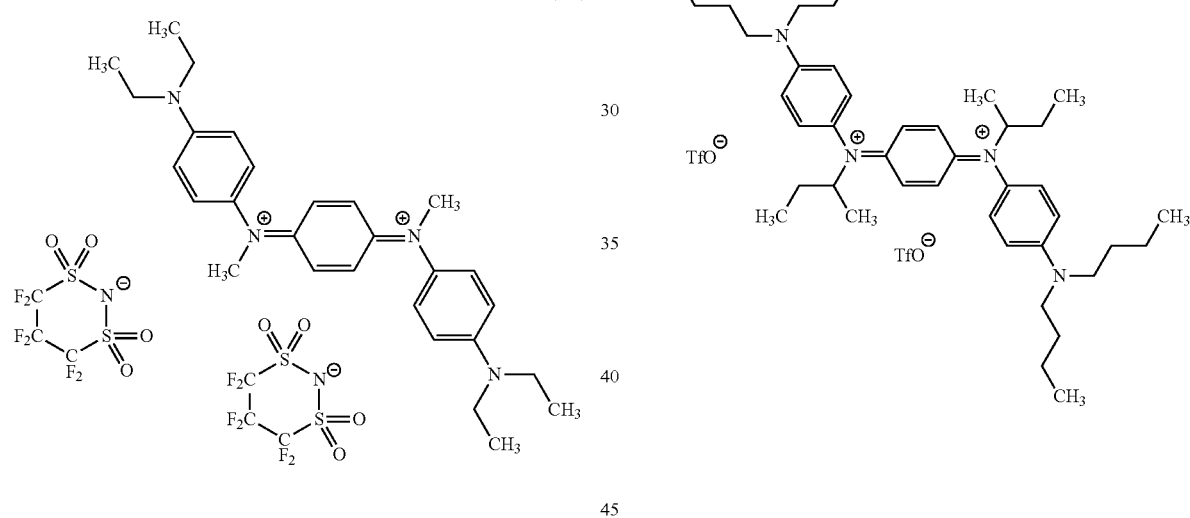
(2-7)
(2-10)
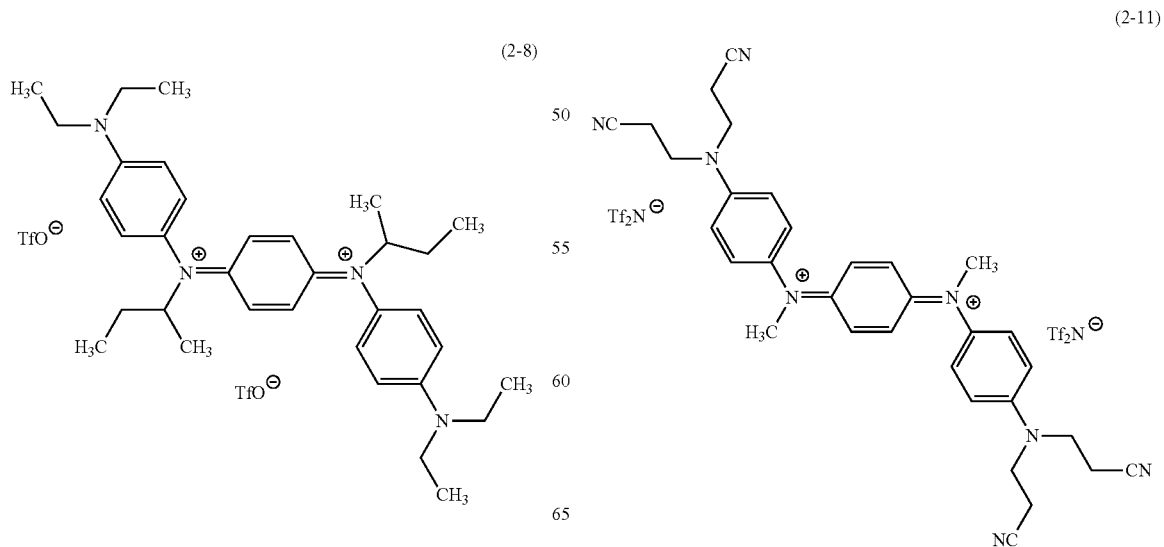
(2-8)
(2-11)

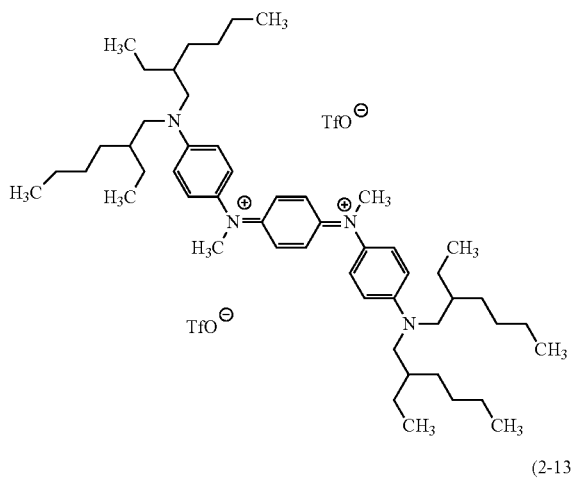

(2-12)

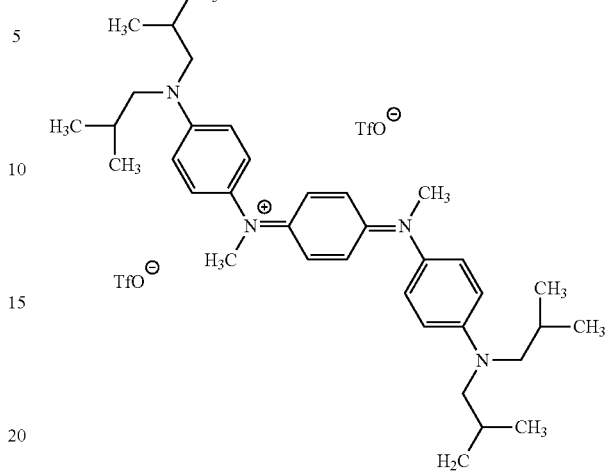

(2-15)

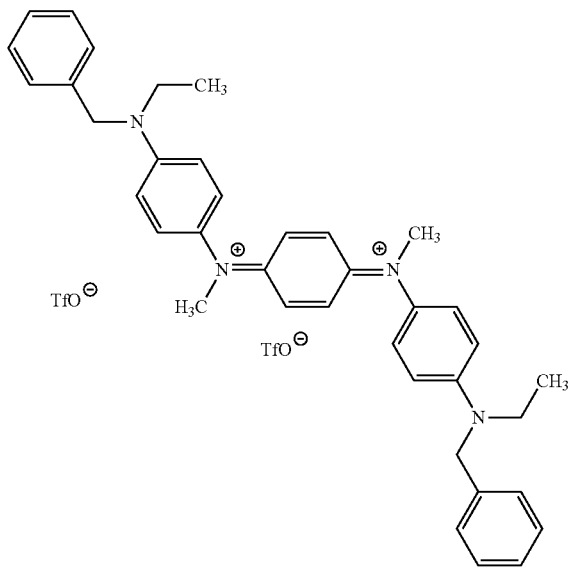

(2-13)

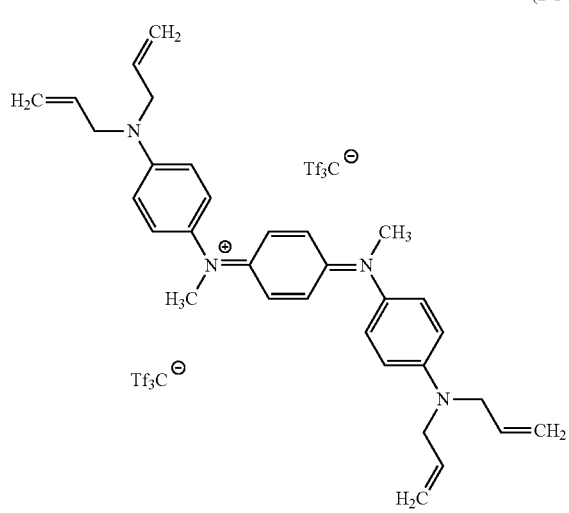

(2-14)

At least one kind of the compound (2-3), (2-4), (2-5), (2-6), (2-8), (2-10), or (2-12) is preferably used from the viewpoint of improving the light fastness of a colored product. At least one kind of the compound (2-3), (2-8), or (2-12) is particularly preferably used.

When the compounds represented by the formula (1) and the formula (2) are used, the compounds may be used alone, or may be used in combination thereof in accordance with a purpose.

The compound according to at least one embodiment of the present disclosure may be used as a liquid composition including a medium having dissolved or dispersed therein the compound. In this case, the incorporation of a colorant into the liquid composition is not essential. When no colorant is incorporated, the effects of the present disclosure may be obtained by bringing a colorant applied onto a substrate and the liquid composition close to each other on the substrate.

<Colorant to be Used in Combination>

The compound according to at least one embodiment of the present disclosure can improve the light fastness of a colorant to be incorporated into, for example, recording paper or a color filter by being brought close to the colorant. Although the colorant is not particularly limited, the effects of the present disclosure are further exhibited when the colorant is a dye. In general, an oily dye referred to as "disperse dye" or "sublimation dye" may be suitably used as the dye. In particular, when the compound is used in combination with an anthraquinone-based dye, a methine-based dye, an azomethine-based dye, or a triphenylmethane-based dye having high chroma, the effects of the present disclosure are exhibited to the largest extent.

Although the usage amount of the compound according to at least one embodiment of the present disclosure is not particularly limited, the compound may be used in an amount in the range of from 0.1 part by mass to 100 parts by mass with respect to 100 parts by mass of the colorant (total number of parts by mass of the colorant). The amount preferably falls within the range of from 0.5 part by mass to 50 parts by mass. In particular, the amount more preferably falls within the range of from 1.0 part by mass to 30 parts by mass.

Each of the compounds represented by the formulae (1) and (2) according to at least one embodiment of the present disclosure has the following feature. That is, the compound has near-infrared absorption having a local maximum absorption wavelength of 900 nm or more and 1,400 nm or less.

Further, the compound has small absorption in a visible region, and hence has substantially no risk of causing a change in color tone of the colorant or the fading thereof.

Next, a liquid composition, a thermal transfer recording sheet, a toner, and a resist composition for a color filter each including the compound represented by the formula (1) or (2) are sequentially described.

<Liquid Composition>

First, the liquid composition according to at least one embodiment of the present disclosure is described. The liquid composition according to at least one embodiment of the present disclosure may be obtained by dispersing or dissolving the compound represented by the formula (1) or (2) in a medium.

Further, the liquid composition is appropriately selected in accordance with its use application.

For example, an additive, such as a colorant, an emulsifying agent, or a resin, may be incorporated into the liquid composition to the extent that the characteristics of the composition in various applications are not impaired.

[Medium]

In the present disclosure, the term "medium" means water or an organic solvent. When the organic solvent is used as the medium, the kind of the organic solvent is selected in accordance with the application of the liquid composition, and is not particularly limited. Examples of the organic solvent include: alcohols, such as methanol, ethanol, denatured ethanol, isopropanol, n-butanol, isobutanol, tert-butanol, sec-butanol, 2-methyl-2-butanol, 3-pentanol, octanol, benzyl alcohol, and cyclohexanol; glycols, such as methyl cellosolve, ethyl cellosolve, diethylene glycol, and diethylene glycol monobutyl ether; ketones, such as acetone, methyl ethyl ketone, and methyl isobutyl ketone; esters, such as ethyl acetate, butyl acetate, ethyl propionate, and cellosolve acetate; aliphatic hydrocarbons, such as hexane, octane, petroleum ether, and cyclohexane; aromatic hydrocarbons, such as benzene, toluene, and xylene; halogenated hydrocarbons, such as carbon tetrachloride, trichloroethylene, and tetrabromoethane; ethers, such as diethyl ether, dimethyl glycol, trioxane, and tetrahydrofuran; acetals, such as methylal and diethyl acetal; organic acids, such as formic acid, acetic acid, and propionic acid; and sulfur or nitrogen-containing organic compounds, such as nitrobenzene, dimethylamine, monoethanolamine, pyridine, dimethyl sulfoxide, and dimethylformamide.

In addition, a polymerizable monomer may be used as the organic solvent. The polymerizable monomer is, for example, an addition-polymerizable monomer or a condensation-polymerizable monomer, and is preferably an addition-polymerizable monomer. Specific examples of the polymerizable monomer include: styrene-based monomers, such as styrene, α-methylstyrene, a-ethylstyrene, o-methylstyrene, m-methylstyrene, p-methylstyrene, o-ethylstyrene, m-ethylstyrene, and p-ethylstyrene; acrylate-based monomers, such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile, and acrylic acid amide; methacrylate-based monomers, such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile, and methacrylic acid amide; olefin-based monomers, such as ethylene, propylene, butylene, butadiene, isoprene, isobutylene, and cyclohexene; vinyl halide-based monomers, such as vinyl chloride, vinylidene chloride, vinyl bromide, and vinyl iodide; vinyl ester-based monomers, such as vinyl acetate, vinyl propionate, and vinyl benzoate; vinyl ether-based monomers, such as vinyl methyl ether, vinyl ethyl ether, and vinyl isobutyl ether; and vinyl ketone-based monomers, such as vinyl methyl ketone, vinyl hexyl ketone, and methyl isopropenyl ketone. Those monomers may be used alone, or may be used in combination thereof as required.

The usage amount of the compound represented by the formula (1) or (2) according to at least one embodiment of the present disclosure is from 0.1 part to 30 parts, preferably from 1 part to 20 parts with respect to the medium.

[Colorant]

A known colorant may be used in combination with the liquid composition according to at least one embodiment of the present disclosure to the extent that the solubility or dispersibility of the compound represented by the formula (1) or (2) according to at least one embodiment of the present disclosure in the medium is not impaired.

Although the colorant is not particularly limited, an oily dye referred to as "disperse dye" or "sublimation dye" may be suitably used. In particular, when the liquid composition is used in combination with, for example, a methine-based dye, an azomethine-based dye, or a triphenylmethane-based dye having high chroma, the effects of the present disclosure are exhibited to the largest extent.

Although the usage amount of the compound according to at least one embodiment of the present disclosure is not particularly limited, the compound may be used in an amount in the range of from 0.1 part by mass to 100 parts by mass with respect to 100 parts by mass of the colorant (total number of parts by mass of the colorant). The amount preferably falls within the range of from 0.5 part by mass to 50 parts by mass. In particular, the amount more preferably falls within the range of from 1.0 part by mass to 30 parts by mass.

[Emulsifying Agent]

When water is used as the medium of the liquid composition according to at least one embodiment of the present disclosure, an emulsifying agent may be added as required for obtaining satisfactory dispersion stability of the colorant. The emulsifying agent is not particularly limited, but examples thereof include a cationic surfactant, an anionic surfactant, and a nonionic surfactant.

Examples of the cationic surfactant include dodecylammonium chloride, dodecylammonium bromide, dodecyltrimethylammonium bromide, dodecylpyridinium chloride, dodecylpyridinium bromide, and hexadecyltrimethylammonium bromide.

Examples of the anionic surfactant include: fatty acid soaps, such as sodium stearate and sodium dodecanoate; and sodium dodecyl sulfate, sodium dodecylbenzene sulfate, and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

[Resin]

The liquid composition according to at least one embodiment of the present disclosure may further include a resin. The kind of the resin is determined in accordance with the purpose and application of the liquid composition, and is not particularly limited. Examples of the resin include the following resins: a styrene-based polymer, an acrylic acid-based polymer, a methacrylic acid-based polymer, a polyester resin, a polyvinyl ether resin, a polyvinyl methyl ether resin, a polyvinyl alcohol resin, a polyvinyl butyral resin, a polyurethane resin, and a polypeptide resin. Those resins may be used alone, or may be used in combination thereof as required.

Although a disperser is not particularly limited, medium-type dispersers, such as a rotary shearing-type homogenizer, a ball mill, a sand mill, and an attritor, and high-pressure counter collision-type dispersers may each be used.

As described above, the liquid composition according to at least one embodiment of the present disclosure includes the compound represented by the formula (1) or (2). Accordingly, the composition has a feature of improving the light fastness of a colored product.

<Thermal Transfer Recording Sheet>

Next, the thermal transfer recording sheet according to at least one embodiment of the present disclosure is described. The compound according to at least one embodiment of the present disclosure may be suitably used in the thermal transfer recording sheet because the compound improves the light fastness of a colored product.

The thermal transfer recording sheet according to at least one embodiment of the present disclosure includes: a substrate; and a coloring material layer obtained by forming a composition containing the compound according to at least one embodiment of the present disclosure into a film on the substrate. The coloring material layer includes at least a yellow layer, a magenta layer, and a cyan layer.

Figure 2A:
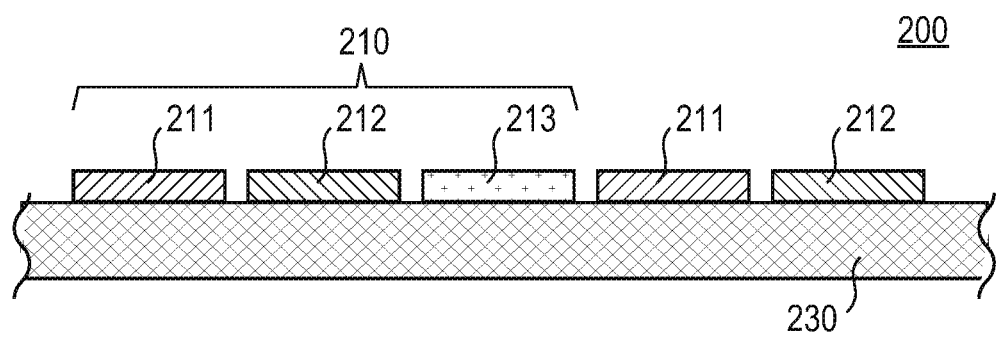
FIG. 2A and FIG. 2B are each a schematic view for illustrating an example of a thermal transfer recording sheet according to at least one embodiment of the present disclosure.

FIG. 2A is an illustration of an example of the thermal transfer recording sheet according to at least one embodiment of the present disclosure. A thermal transfer recording sheet 200 illustrated in FIG. 2A includes a substrate 230 and coloring material layers 210 on the substrate 230. The coloring material layers 210 include a yellow layer 211, a magenta layer 212, and a cyan layer 213 horizontally.

In a thermal transfer recording method, the thermal transfer recording sheet is heated with a heating unit, such as a thermal head, under a state in which the coloring material layers of the thermal transfer recording sheet and a coloring material receiving layer arranged on the surface of an image receiving sheet are superimposed on each other. With such procedure, a coloring material in each of the coloring material layers of the thermal transfer recording sheet is transferred onto the coloring material receiving layer of the image receiving sheet. Thus, image formation is performed.

The coloring material layer (at least one layer selected from the group consisting of a yellow layer, a magenta layer and a cyan layer) contains the compound represented by the formula (1) or (2), the coloring material, a binder resin, a surfactant and a wax to be used as required, and a medium. Although a method of producing the thermal transfer recording sheet according to at least one embodiment of the present disclosure is not particularly limited, the sheet is typically obtained as described below.

The compound represented by the formula (1) or (2), the coloring material, and the binder resin, and as required, the surfactant and the wax are gradually added to the medium while the medium is stirred, and the components are sufficiently conformed to the medium. Subsequently, the composition is stably dissolved, or dispersed in a fine particulate manner, in the medium by applying a mechanical shear force through use of a disperser. Thus, a dispersed liquid (ink) is prepared. The dispersed liquid is applied to a base film that is the substrate, and is dried to form each of the coloring material layers. Further, a transferable protective layer, a heat-resistant slipping layer, or the like to be described later is formed as required. Thus, the thermal transfer recording sheet according to at least one embodiment of the present disclosure is obtained. The thermal transfer recording sheet according to at least one embodiment of the present disclosure is not limited to a thermal transfer recording sheet produced by the production method. The respective components to be used in each of the coloring material layers are described in detail below.

[Coloring Material]

The colorant suitable for the present disclosure described in the foregoing, that is, the high-chroma dye, such as a methine-based dye, an azomethine-based dye, or a triphenylmethane-based dye, is preferred as a coloring material to be used for thermal transfer recording. A methine-based dye or an azomethine-based dye is more preferred. In the thermal transfer recording sheet, a dye having a sublimation property out of the dyes is used. The coloring materials may be used alone or in combination thereof. The usage amount of the coloring material is from 1 part by mass to 150 parts by mass with respect to 100 parts by mass of the binder resin in each of the coloring material layers, and is preferably from 50 parts by mass to 120 parts by mass from the viewpoint of the dispersibility of the coloring material in the dispersed liquid. When two or more kinds of coloring materials are used as a mixture, their total amount preferably falls within the range.

Although the usage amount of the compound represented by the formula (1) or (2) is not particularly limited, the compound may be used in an amount in the range of from 0.1 part by mass to 100 parts by mass with respect to 100 parts by mass of the coloring material (total number of parts by mass of the coloring material). The amount preferably falls within the range of from 0.5 part by mass to 50 parts by mass. In particular, the amount more preferably falls within the range of from 1.0 part by mass to 30 parts by mass.

[Binder Resin]

Although the binder resin is not particularly limited, the resin is preferably any one of the following resins: water-soluble resins, such as a cellulose resin, a polyacrylic acid resin, a starch resin, and an epoxy resin; and organic solvent-soluble resins, such as a polyacrylate resin, a polymethacrylate resin, a polystyrene resin, a polycarbonate resin, a polyether sulfone resin, a polyvinyl butyral resin, an ethyl cellulose resin, an acetyl cellulose resin, a polyester resin, an AS resin, and a phenoxy resin. Those resins may be used alone, or may be used in combination thereof as required.

[Surfactant]

A surfactant may be added to the thermal transfer recording sheet according to at least one embodiment of the present disclosure for imparting sufficient lubricity at the time of the heating of a thermal head (at the time of printing). Examples of the surfactant include a cationic surfactant, an anionic surfactant, and a nonionic surfactant.

Examples of the cationic surfactant include dodecylammonium chloride, dodecylammonium bromide, dodecyltrimethylammonium bromide, dodecylpyridinium chloride, dodecylpyridinium bromide, and hexadecyltrimethylammonium bromide.

Examples of the anionic surfactant include fatty acid soaps, such as sodium stearate and sodium dodecanoate, sodium dodecyl sulfate, sodium dodecylbenzene sulfate, and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

[Wax]

A wax may be added to the thermal transfer recording sheet according to at least one embodiment of the present disclosure for imparting sufficient lubricity at the time of the non-heating of the thermal head. Examples of the wax that may be added include, but not limited to, a polyethylene wax, a paraffin wax, and a fatty acid ester wax.

In addition to the above-mentioned additives, a UV absorber, an antiseptic, an antioxidant, an antistatic agent, a viscosity modifier, and the like may each be added to the thermal transfer recording sheet according to at least one embodiment of the present disclosure as required.

[Medium]

The medium to be used in the preparation of a dispersed body at the time of the formation of each of the coloring material layers is not particularly limited, but is, for example, water or an organic solvent. The organic solvent is preferably any one of: alcohols, such as methanol, ethanol, isopropanol, and isobutanol; cellosolves, such as methyl cellosolve and ethyl cellosolve; aromatic hydrocarbons, such as toluene, xylene, and chlorobenzene; esters, such as ethyl acetate and butyl acetate; ketones, such as acetone, methyl ethyl ketone, methyl isobutyl ketone, and cyclohexanone; halogenated hydrocarbons, such as methylene chloride, chloroform, and trichloroethylene; ethers, such as tetrahydrofuran and dioxane; and N,N-dimethylformamide and N-methylpyrrolidone. Those organic solvents may be used alone, or may be used in combination thereof as required.

[Substrate]

Next, the substrate for forming the thermal transfer recording sheet is described. The substrate supports the coloring material layers, and a known substrate may be used without any particular limitation as long as the substrate is a film having some degree of heat resistance and some degree of strength. Examples thereof include a polyethylene terephthalate film, a polyethylene naphthalate film, a polycarbonate film, a polyimide film, a polyamide film, an aramid film, a polystyrene film, a 1,4-polycyclohexylenedimethylene terephthalate film, a polysulfone film, a polypropylene film, a polyphenylene sulfide film, a polyvinyl alcohol film, cellophane, a cellulose derivative, a polyethylene film, a polyvinyl chloride film, a nylon film, condenser paper, and paraffin paper. Of those, a polyethylene terephthalate film is preferred from the viewpoints of mechanical strength, solvent resistance, and economical efficiency.

The thickness of the substrate is from 0.5 µm to 50 µm, and is preferably from 3 µm to 10 µm from the viewpoint of transferability.

When a dye ink is applied for forming each of the coloring material layers on the substrate, the wettability, adhesive property, and the like of an application liquid are liable to be insufficient. Accordingly, the surface (formation surface) of the substrate on which the coloring material layers are formed is preferably subjected to an adhesion treatment as required. The surface on which the coloring material layers are formed may be one surface of the substrate, or may be each of both surfaces thereof. The adhesion treatment is not particularly limited, but examples thereof may include an ozone treatment, a corona discharge treatment, a UV treatment, a plasma treatment, a low-temperature plasma treatment, a primer treatment, and a chemical treatment. In addition, those treatments may be performed in combination thereof.

As the adhesion treatment for the substrate, an adhesion layer may be applied onto the substrate. The adhesion layer is not particularly limited, but for example, the following materials may each be used: fine particles of an organic material, such as a polyester resin, a polystyrene resin, a polyacrylic acid ester resin, a polyamide resin, a polyether resin, a polyvinyl acetate resin, a polyethylene resin, a polypropylene resin, a polyvinyl chloride resin, a polyvinyl alcohol resin, or a polyvinyl butyral resin; and fine particles of an inorganic material, such as silica, alumina, magnesium carbonate, magnesium oxide, or titanium oxide.

The compound represented by the formula (1) or (2) may be incorporated into the protective layer of the thermal transfer recording sheet according to at least one embodiment of the present disclosure.

Figure 2B:
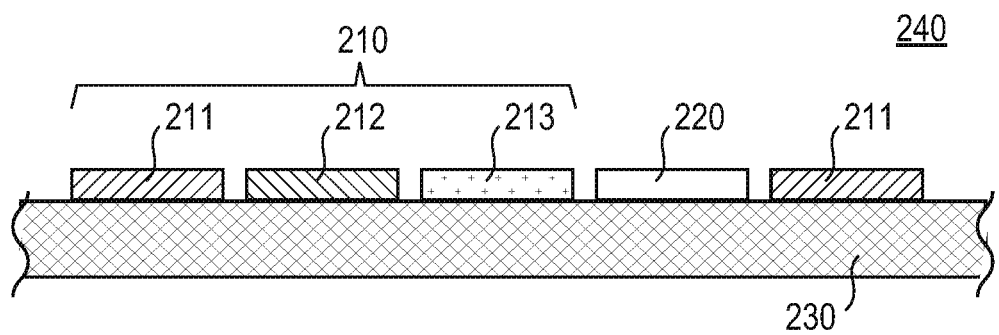

FIG. 2B is an illustration of an example of the thermal transfer recording sheet according to at least one embodiment of the present disclosure. A thermal transfer recording sheet 240 illustrated in FIG. 2B includes the substrate 230, and the coloring material layers 210 and a protective layer 220 on the substrate 230. The coloring material layers 210 include the yellow layer 211, the magenta layer 212, and the cyan layer 213 field sequentially. In addition, the coloring material layers 210 and the protective layer 220 are formed field sequentially. The protective layer 220 contains the compound represented by the formula (1) or (2). When the protective layer contains the compound represented by the formula (1) or (2), the protective layer contains at least one or more kinds of compounds selected from the group consisting of the compounds each represented by the formula (1) or (2). Also in the case where the compound represented by the formula (1) or (2) is incorporated into the protective layer, the same effects as those in the case where the compound represented by the formula (1) or (2) is incorporated into each of the coloring material layers can be obtained.

Although the binder resin to be used in the protective layer is not particularly limited, the resin is preferably any one of the following resins: synthetic resins, including polystyrene, acrylic resins, such as polymethyl methacrylate and polyethyl acrylate, styrene-based resins, such as poly-a-methylstyrene, vinyl-based resins, such as polyvinyl chloride, polyvinyl acetate, a vinyl chloride-vinyl acetate copolymer, polyvinyl butyral, and polyvinyl acetal, a polyamide resin, an epoxy resin, a polyurethane resin, a petroleum resin, an ionomer, an ethylene-acrylic acid copolymer, and an ethylene-acrylate copolymer.

The usage amount of the compound represented by the formula (1) or (2) to be used in the present disclosure is preferably from 0.1 part by mass to 50 parts by mass with respect to 100 parts by mass of the binder resin, and is more preferably from 0.5 part by mass to 20 parts by mass from the viewpoints of the color of a printed product and an improvement in light fastness thereof.

The thickness of the layer is preferably from about 0.1 µm to about 5 µm.

In addition, a peeling layer, which contains, for example, an acrylic resin, such as polymethyl methacrylate or polyethyl acrylate, and has a thickness of from about 0.1 µm to about 1.5 µm, is more preferably arranged below the layer containing the compound for facilitating the peeling of the substrate from the sheet.

The layer is formed on the substrate layer described in the foregoing.

The thermal transfer recording protective sheet according to at least one embodiment of the present disclosure contains the compound represented by the formula (1) or (2), and hence a thermal transfer recording sheet improved in light fastness of a colored product can be provided.

<Toner>

Next, the toner according to at least one embodiment of the present disclosure is described. The compound according to at least one embodiment of the present disclosure may be suitably used in the toner because the compound improves the light fastness of a colored product.

The toner according to at least one embodiment of the present disclosure includes, for example, the compound represented by the formula (1) or (2), a colorant, and a binder resin, and as required, a magnetic substance, a wax, a charge control agent, or any other additive.

The colorants may be used alone or in combination thereof as long as the colorants are each a colorant typically used in a toner. In addition, in accordance with a method of producing the toner, the colorant may be used in combination with a known pigment or dye for adjusting, for example, the color tone of the toner. In particular, the effects of the present disclosure are exhibited when the dye is used as the colorant of the toner in addition to the pigment.

In general, an oily dye referred to as "disperse dye" or "sublimation dye" may be suitably used as the dye. In particular, when the compound represented by the formula (1) or (2) is used in combination with a high-chroma dye, such as a methine-based, azomethine-based, or triphenylmethane-based dye, the effects of the present disclosure are exhibited to the largest extent.

Although the usage amount of the compound represented by the formula (1) or (2) according to at least one embodiment of the present disclosure is not particularly limited, the compound may be used in an amount in the range of from 0.1 part by mass to 100 parts by mass with respect to 100 parts by mass of the colorant to be used (total number of parts by mass of the colorant). The amount preferably falls within the range of from 0.5 part by mass to 50 parts by mass. In particular, the amount more preferably falls within the range of from 1.0 part by mass to 30 parts by mass.

The compound according to at least one embodiment of the present disclosure is suitable for each of a pulverized toner and a toner for liquid development. The pulverized toner is produced by: melting and kneading the colorant and the like in the binder resin; finely pulverizing the kneaded product with a fine pulverization apparatus; and classifying the finely pulverized product with a classifier to provide toner particles each having a desired particle diameter. The toner for liquid development is obtained by dispersing or dissolving coloring resin powder (toner), and as required, an assistant, such as a charge control agent or a wax, in an electrically insulating carrier liquid.

<Color Filter>

A color filter including a resist layer containing the compound represented by the formula (1) or (2) is described below.

In a color filter obtained by arraying two or more kinds of pixels having different spectroscopic characteristics so that the pixels may be adjacent to each other, a resist composition for a color filter including the compound according to at least one embodiment of the present disclosure and a coloring material is used in a pixel for forming at least one color out of the colors (e.g., red, green, and blue colors) of the plurality of pixels. Thus, a color filter having high color developability and excellent light fastness can be obtained.

Although a method of forming each colored pixel is not particularly limited, the formation may be performed by, for example, an inkjet method, a printing method, or a photolithography method.

When the inkjet method is used, a colored layer is formed by: forming a black matrix on a glass substrate; injecting the resist composition for a color filter as an ink into an opening portion of the black matrix with an inkjet apparatus to color the matrix; and subjecting the resultant to a heating treatment.

A water repellent, such as silicon or fluorine, or the like may be added to the black matrix.

When the printing method is used, the colored pixel is formed by applying and drying the resist composition for a color filter. When the photolithography method is used, the colored pixel is formed by: applying the resist composition onto a transparent substrate so that its thickness at the time of drying may be from 0.1 µm to 20 µm, preferably from 0.5 µm to 5 µm; and drying the composition.

Next, the resist composition for a color filter according to at least one embodiment of the present disclosure (hereinafter sometimes referred to as "resist composition according to at least one embodiment of the present disclosure") is described.

The resist composition for a color filter according to at least one embodiment of the present disclosure includes a binder resin, a medium, a colorant, and the compound according to at least one embodiment of the present disclosure. Conventionally known products may be used as the binder resin and the medium in accordance with a production method for, and the application of, a color filter to be used. The colorant is not particularly limited as long as the colorant is a colorant that may be typically used in a resist composition for a color filter. However, when the compound is used in combination with the colorant suitable for the present disclosure described in the foregoing, that is, the high-chroma dye, such as a methine-based, azomethine-based, or triphenylmethane-based dye, the effects of the present disclosure are exhibited to the largest extent.

Although the usage amount of the compound represented by the formula (1) or (2) is not particularly limited, the compound may be used in an amount in the range of from 0.1 part by mass to 100 parts by mass with respect to 100 parts by mass of the colorant to be used (total number of parts by mass of the colorant). The amount preferably falls within the range of from 0.5 part by mass to 50 parts by mass. In particular, the amount more preferably falls within the range of from 1.0 part by mass to 30 parts by mass.

EXAMPLES

The present disclosure is described in more detail below by way of Examples and Comparative Examples. However, the present disclosure is not limited to the examples. In the following description, the terms "part(s)" and "%" represent "part(s) by mass" and "mass %", respectively unless otherwise stated. In addition, a $^1$H nuclear magnetic resonance spectroscopic analysis ($^1$H-NMR) apparatus (AVANCE-600 NMR SPECTROMETER, manufactured by Bruker), a high performance liquid chromatograph mass spectrometer (LCMS-2010, manufactured by Shimadzu Corporation), and a TG-DTA (STA7200RV, manufactured by Hitachi High-Tech Science Corporation) were used as analyzers.

Production Example 1: Production of Compound (1-3)]

The following materials were added to a solution of N,N-dimethylphenylenediamine (A-1) (3.3 g, 24 mmol) in 20 mL of toluene, and the resultant was subjected to nitrogen purging.

Palladium acetate (0.5 g, 2.4 mmol)
2-(Di-tert-dibutylphosphino)biphenyl (0.72 g, 2.4 mmol)
Halide (B-4) (15.1 g, 53 mmol)
Sodium tert-butoxide (6.9 g, 72 mmol)

Under a nitrogen atmosphere, the temperature of the solution was increased, and the solution was stirred at 100° C. for 4 hours. After the completion of the reaction, the mixture was cooled to room temperature, and was subjected to celite filtration. The filtrate was washed with 50 mL of a saturated saline solution, and the organic layer was concentrated under reduced pressure. The residue was purified by silica gel column chromatography (developing solvent: ethyl acetate/heptane) to provide the corresponding compound (C-1) (11.3 g, 86.7%). The compound (C-1) was identified by $^1$H-NMR analysis and mass spectrometry.

A solution of silver(I) trifluoromethanesulfonate (0.47 g, 1.8 mmol) in 50 mL of acetone was slowly dropped into a solution of the compound (C-1) (1.0 g, 1.8 mmol) obtained in the foregoing in 50 mL of acetone.

The mixture was stirred at room temperature for 1 hour, and the produced silver salt was subjected to celite filtration. The resultant filtrate was concentrated under reduced pressure, and was dried in a vacuum to quantitatively provide a target compound (1-3).

Production Examples 2 and 3: Production of Compounds (1-8) and (1-10)]

The compounds (1-8) and (1-10) were each produced by the same method as that of Production Example 1 except that: the diamino compound (A-5) was used instead of the diamino compound (A-1); and the halide (B-2) or (B-4) was used instead of the halide (B-4).

Production Examples 4 to 6: Production of Compounds (2-3), (2-8), and (2-10)]

The compounds (2-3), (2-8), and (2-10) were produced by the same methods as those of Production Examples 1 to 3, respectively except that in Production Examples 1 to 3, the usage amount of silver(I) trifluoromethanesulfonate was changed to a value twice as large as the original value.

<Liquid Composition Production Example>

A liquid composition according to at least one embodiment of the present disclosure and a comparative liquid composition were produced by the following methods.

[Production of Liquid Composition (1)]

3 Parts of the compound (1-3) synthesized in Production Example 1 and 15 parts of an azomethine-based dye A were dissolved in 90 parts of a 1:1 mixed solvent of methyl ethyl ketone and toluene. 15 Parts of a polyvinyl butyral resin (product name: DENKA 3000-K, manufactured by Denki Kagaku Kogyo K.K.) was gradually added to the resultant solution while the solution was stirred. Thus, a liquid composition (1) was obtained.

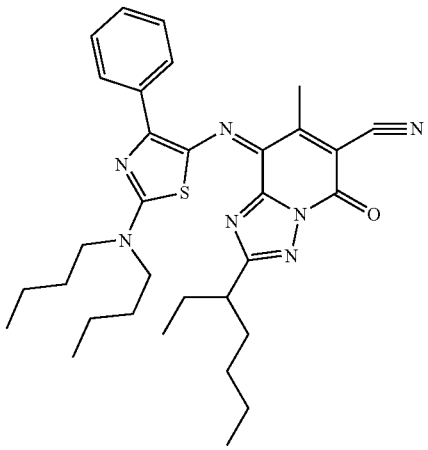

Azomethine-based dye A

[Production of Liquid Compositions (2) to (8)]

Liquid compositions (2) to (8) were each produced in the same manner as in the production of the liquid composition (1) except that in the production of the liquid composition (1), the compound (1-3) and the azomethine-based dye A (dye A) were changed to a compound and a dye shown in Table 1, respectively. In addition, the structures of an azomethine dye B (dye B) and a methine dye C (dye C) are represented below.

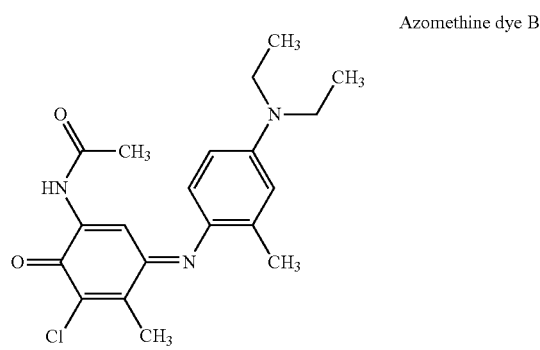

Azomethine dye B

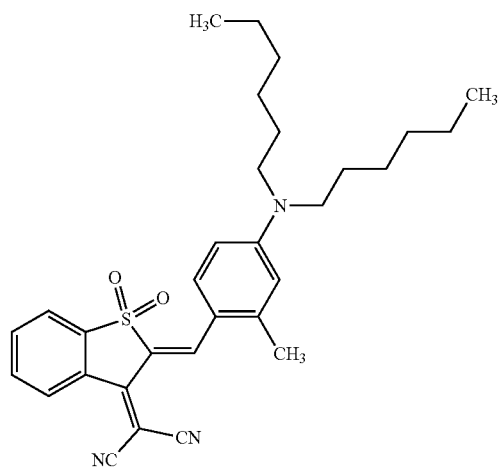

Methine dye C

Comparative Examples 1 to 5: Production of Comparative Liquid Compositions (1) to (5)

Comparative liquid compositions (1) to (5) were each produced in the same manner as in the production of the liquid composition (1) except that in the production of the liquid composition (1), the compound (1-3) and the azomethine-based dye A were changed to any one of the following comparative compounds (1) to (3) and a dye shown in Table 1, respectively.

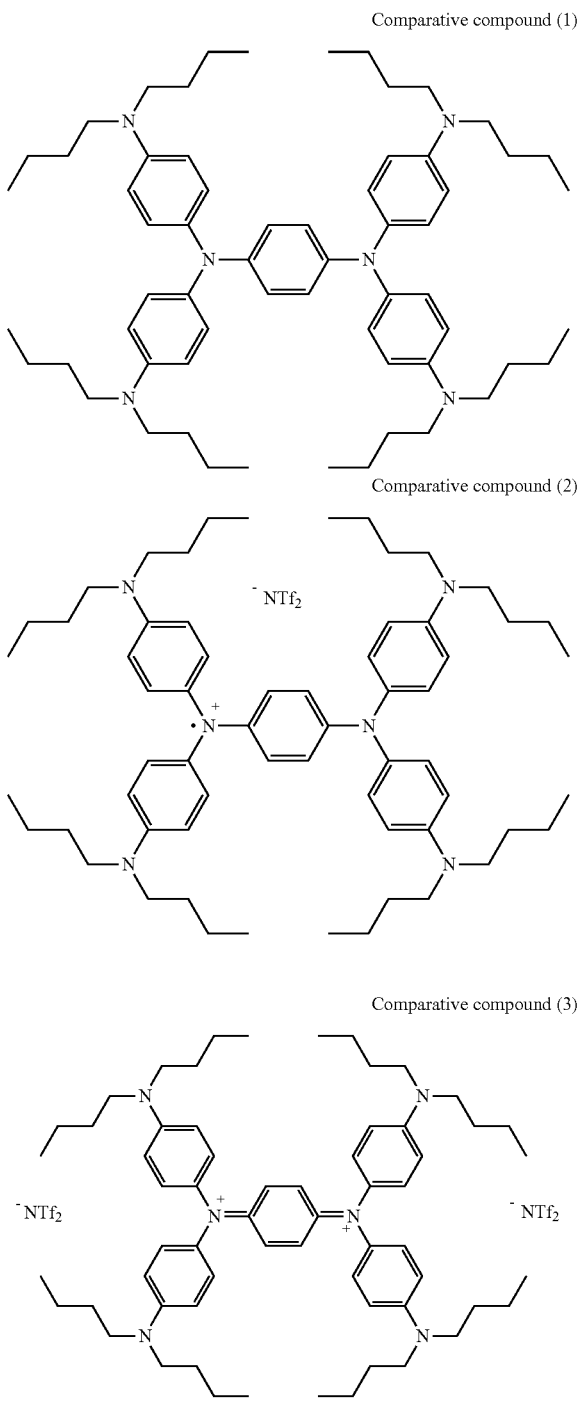

Examples 1 to 8 and Comparative Examples 1 to 5

[Production of Image Sample for Bar Coat Light Fastness Evaluation]

Each of the liquid compositions (1) to (8) and the comparative liquid compositions (1) to (5) produced in the foregoing was applied to hiding ratio-measuring paper by a bar coating method (number of the annealing wire of a bar coater: No. 10), and was then air-dried overnight to produce an image sample for a light fastness evaluation.

[Light Fastness Evaluation]

The image sample was loaded into a xenon test apparatus (ATLAS WEATHER-OMETER Ci4000, manufactured by Toyo Seiki Seisaku-sho, Ltd.), and was exposed under the following conditions for 20 hours.

Illuminance: 0.28 $W/m^2$ at 340 nm

Black panel temperature: 40° C., relative humidity: 50%

Then, the cyan optical density (O.D.) of the sample after the exposure (after the light fastness test) and that of a reference sample (Comparative Example 4 or 5), which contained the same dye and was free of the compound according to at least one embodiment of the present disclosure, after the exposure were compared to each other.

Light fastness improvement (%)=(OD1/OD2)×100

OD1: The O.D. of the sample containing the compound according to at least one embodiment of the present disclosure or a comparative compound after the light fastness test OD2: The O.D. of the reference sample, which contains the same dye and is free of the compound according to at least one embodiment of the present disclosure, after the light fastness test Evaluation criteria are as described below.

A: 150<Light fastness improvement (%)

B: 101<Light fastness improvement (%)≤150

C: Light fastness improvement (%)≤101

The obtained results are shown in Table 1. When the light fastness improvement (%) was more than 101, it was judged that the effects of the present disclosure were obtained, and when the light fastness improvement (%) was more than 150, it was judged that the improvement was at the level at which the effects of the present disclosure were sufficiently obtained.

[Evaluation of Storage Stability of Ink]

Each of the liquid compositions (1) to (8) and the comparative liquid compositions (1) to (5) was hermetically sealed, and was stored at a temperature of 10° C. for 1 month, followed by the visual observation of the presence or absence of an aggregate after the storage. The results are shown in Table 1.

Evaluation criteria are as described below.

A: Substantially no aggregate of the compound is observed (storage stability is extremely excellent).

B: The aggregate of the compound is observed to some extent (storage stability is excellent).

C: The aggregate of the compound is considerably observed (storage stability is poor).

TABLE 1

|  | Compound | Dye | Light fastness (bar coat) | | Liquid storage stability |
|---|---|---|---|---|---|
|  |  |  | Light fastness improvement (%) | Evaluation |  |
| Example 1 | Liquid composition (1) | 1-3 | Dye A | 250% | A | A |
| Example 2 | Liquid composition (2) | 1-8 | C.I. Solvent Blue 5 | 195% | A | A |
| Example 3 | Liquid composition (3) | 1-10 | C.I. Solvent Blue 5 | 180% | A | A |
| Example 4 | Liquid composition (4) | 2-3 | Dye A | 230% | A | A |
| Example 5 | Liquid composition (5) | 2-8 | Dye A | 140% | B | A |
| Example 6 | Liquid composition (6) | 2-10 | Dye A | 160% | A | A |
| Example 7 | Liquid composition (7) | 1-3 | Dye B | 145% | B | A |
| Example 8 | Liquid composition (8) | 1-8 | Dye C | 155% | A | A |
| Comparative Example 1 | Comparative liquid composition (1) | Comparative compound 1 | C.I. Solvent Blue 5 | 99% | C | C |
| Comparative Example 2 | Comparative liquid composition (2) | Comparative compound 2 | C.I. Solvent Blue 5 | 98% | C | B |
| Comparative Example 3 | Comparative liquid composition (3) | Comparative compound 3 | C.I. Solvent Blue 5 | 110% | B | C |
| Comparative Example 4 | Comparative liquid composition (4) |  | Dye A | 100% | C | A |
| Comparative Example 5 | Comparative liquid composition (5) |  | C.I. Solvent Blue 5 | 100% | C | A |

As shown in Table 1, when a liquid composition includes the compound according to at least one embodiment of the present disclosure, its light fastness is excellent and its storage stability is satisfactory.

Examples 9 to 16 and Comparative Examples 6 to 10

[Production of Image Sample for Sublimation Print Light Fastness]

Each of the liquid compositions (1) to (8) and the comparative liquid compositions (1) to (5) was applied onto a polyethylene terephthalate film having a thickness of 4.5 μm (LUMIRROR (trademark); manufactured by Toray Industries, Inc.) so that its thickness after drying became 1 μm, followed by drying. Thus, thermal transfer recording sheets (1) to (8) and comparative thermal transfer recording sheets (1) to (5) were produced.

Each of the thermal transfer recording sheets (1) to (8) and the comparative thermal transfer recording sheets (1) to (5) was transferred onto printing paper with a reconstructed machine of a photo printer SELPHY manufactured by Canon Inc. to produce an image sample.

[Light Fastness Evaluation]

The image sample was loaded into a xenon test apparatus (ATLAS WEATHER-OMETER Ci4000, manufactured by Toyo Seiki Seisaku-sho, Ltd.), and was exposed under the following conditions for 20 hours.

Illuminance: 0.28 W/m² at 340 nm

Black panel temperature: 40° C., relative humidity: 50%

Then, the cyan optical density (O.D.) of the sample after the exposure (after the light fastness test) and that of a reference sample (Comparative Example 9 or 10), which contained the same dye and was free of the compound according to at least one embodiment of the present disclosure, after the exposure were compared to each other.

Light fastness improvement (%)=(OD1/OD2)×100

OD1: The O.D. of the sample containing the compound according to at least one embodiment of the present disclosure or a comparative compound after the light fastness test OD2: The O.D. of the reference sample, which contains the same dye and is free of the compound according to at least one embodiment of the present disclosure, after the light fastness test Evaluation criteria are as described below.

A: 150<Light fastness improvement (%)
B: 101<Light fastness improvement (%)≤150
C: Light fastness improvement (%)≤101

The obtained results are shown in Table 2. When the light fastness improvement (%) was more than 101, it was judged that the effects of the present disclosure were obtained, and when the light fastness improvement (%) was more than 150, it was judged that the improvement was at the level at which the effects of the present disclosure were sufficiently obtained.

TABLE 2

|  |  | Compound | Dye | Light fastness (sublimation print) | |
|---|---|---|---|---|---|
|  |  |  |  | Light fastness improvement (%) | Evaluation |
| Example 9 | Liquid composition (9) | 1-3 | Dye A | 220% | A |

TABLE 2-continued

| | Compound | Dye | Light fastness (sublimation print) Light fastness improvement (%) | Evaluation |
|---|---|---|---|---|
| Example 10 | Liquid composition (10) | 1-8 | C.I. Solvent Blue 5 | 165% | A |
| Example 11 | Liquid composition (11) | 1-10 | C.I. Solvent Blue 5 | 155% | A |
| Example 12 | Liquid composition (12) | 2-3 | Dye A | 204% | A |
| Example 13 | Liquid composition (13) | 2-8 | Dye A | 130% | B |
| Example 14 | Liquid composition (14) | 2-10 | Dye A | 153% | A |
| Example 15 | Liquid composition (15) | 1-3 | Dye B | 165% | A |
| Example 16 | Liquid composition (16) | 1-8 | Dye C | 153% | A |
| Comparative Example 6 | Comparative liquid composition (1) | Comparative compound 1 | C.I. Solvent Blue 5 | 98% | C |
| Comparative Example 7 | Comparative liquid composition (2) | Comparative compound 2 | C.I. Solvent Blue 5 | 99% | C |
| Comparative Example 8 | Comparative liquid composition (3) | Comparative compound 3 | C.I. Solvent Blue 5 | 105% | B |
| Comparative Example 9 | Comparative liquid composition (4) | | Dye A | 100% | C |
| Comparative Example 10 | Comparative liquid composition (5) | | C.I. Solvent Blue 5 | 100% | C |

Example 17

[Production of Protective Layer Sheet]

3 Parts of the compound (1-3) synthesized in Production Example 1 was added to 90 parts of a 1:1 mixed solvent of methyl ethyl ketone and toluene to obtain a mixture. Thereafter, 15 parts of a polyvinyl butyral resin (product name: DENKA 3000-K, manufactured by Denki Kagaku Kogyo K.K.) was gradually added to the mixture while the mixture was stirred. Thus, a liquid composition (12) was obtained.

A polyethylene terephthalate film having a thickness of 4.5 μm (LUMIRROR; manufactured by Toray Industries, Inc.) was used as a substrate, and the liquid composition (12) was applied onto the substrate so that its thickness after drying became 0.5 μm, followed by drying. Thus, a protective layer sheet was produced.

[Production of Image Sample]

The produced protective layer sheet was printed onto the image sample of Comparative Example 10 (free of the compound according to at least one embodiment of the present disclosure) with a reconstructed machine of a photo printer SELPHY manufactured by Canon Inc. to provide an evaluation sample.

[Light Fastness Evaluation]

The above-mentioned sample was loaded into a xenon test apparatus (ATLAS WEATHER-OMETER Ci4000, manufactured by Toyo Seiki Seisaku-sho, Ltd.), and was exposed under the following conditions for 20 hours, followed by the comparison of the cyan O.D. of the sample after the exposure and that of the image sample of Comparative Example 10 after the exposure.

Illuminance: 0.28 W/m² at 340 nm

Black panel temperature: 40° C., relative humidity: 50%

The cyan O.D. of the printed sample containing the compound according to at least one embodiment of the present disclosure after the exposure was 1.8 times as high as that of Comparative Example 10, and hence it was confirmed that the application of the compound according to at least one embodiment of the present disclosure as a protective layer markedly improved the light fastness of the image sample.

Example 18

[Production of Toner]

A toner was produced by the following method.

Binder resin (polyester resin): 100 parts by mass (glass transition temperature Tg: 55° C., acid value: 20 mgKOH/g, hydroxyl value: 16 mgKOH/g, main peak molecular weight Mp: 4,500, number-average molecular weight Mn: 2,300, weight-average molecular weight Mw: 38,000)

| | |
|---|---|
| C.I. Pigment Blue 15:3 | 5 parts by mass |
| Compound (1-8): | 0.5 part by mass |
| C.I. Solvent Blue 5 | 0.5 part by mass |
| Aluminum 1,4-di-t-butyl salicylate compound: | 0.5 part by mass |
| Paraffin wax (maximum endothermic peak temperature: 78° C.): | 5 parts by mass |

The materials were mixed well with each other by using a Henschel mixer (product name: MODEL FM-75J, manufactured by Mitsui Mining Co., Ltd.). After that, the mixture was kneaded with a twin-screw kneader (product name: MODEL PCM-45, manufactured by Ikegai Ironworks Corporation) having a set temperature of 130° C. in a feeding amount of 60 kg/hr. The temperature of the kneaded product at the time of its ejection was about 150° C. The resultant kneaded product was cooled, and was coarsely pulverized with a hammer mill, followed by fine pulverization with a mechanical pulverizer (product name: T-250, manufactured by Turbo Kogyo Co., Ltd.) in a feeding amount of 20 kg/hr. Further, the resultant finely pulverized product was classified with a multi-division classifier utilizing a Coanda effect to provide toner particles.

2 Parts by mass of silica fine particles were externally added to 100 parts by mass of the resultant toner particles with a Henschel mixer to provide a toner (1). The resultant toner (1) had a weight-average particle diameter (D4) of about 6.0 contained 29.0 number % of particles each having a particle diameter of 4.1 μm or less, and contained 0.8 vol % of particles each having a particle diameter of 10.1 μm or more.

A fixed image of the toner (1) having a laid-on level of 0.45 mg/cm² was produced on CLC color copier paper (manufactured by Canon Inc.) with a reconstructed machine of LBP-5300 (product name, manufactured by Canon Inc.). The fixed image was subjected to the same light fastness test as those of Examples 1 to 8. As a result, the ratio of the cyan O.D. of the image after the light fastness test to that of an image, which had the same colorant composition and was free of the compound according to at least one embodiment of the present disclosure, was 154%. Thus, it was confirmed that the incorporation of the compound according to at least one embodiment of the present disclosure provided excellent light fastness.

Example 19

[Production of Color Filter]

A resist composition for a color filter and a color filter were produced by the following methods.

6 Parts of the compound (2-10) synthesized in Production Example 6 and 12 parts of C.I. Solvent Blue 5 were mixed with 120 parts of cyclohexanone, and were dispersed therein for 1 hour with an attritor (manufactured by Mitsui Mining Co., Ltd.) to provide an ink (1) for a resist composition.

Subsequently, 22 parts of the ink (1) for a resist composition was slowly added to a solution containing the following materials, and the mixture was stirred at room temperature for 3 hours.

| | |
|---|---|
| Acrylic copolymer composition having a monomer ratio of 40 mass % of n-butyl acrylate, 30 mass % of acrylic acid, and 30 mass % of hydroxyethyl methacrylate (weight-average molecular weight Mw: 10,000) | 6.7 parts by mass |
| Dipentaerythritol pentaacrylate: | 1.3 parts by mass |
| 2-Benzyl-2-dimethylamino-1-(4-morpholinophenyl)-butanone (polymerization initiator): | 0.4 part by mass |
| Cyclohexanone: | 96 parts by mass |

After the stirring, the mixture was filtered with a 1.5-micrometer filter to provide a resist composition (1) for a color filter.

The resist composition (1) for a color filter was applied onto a glass substrate by spin coating, and was dried at 90° C. for 3 minutes, followed by the exposure of its entire surface to light. The resultant was post-cured at 180° C. to produce a color filter (1).

The color filter was subjected to the same light fastness test as those of Examples 1 to 8. As a result, the ratio of the cyan O.D. of the filter after the light fastness test to that of a color filter, which had the same colorant composition and was free of the compound according to at least one embodiment of the present disclosure, was 170%. In other words, it was confirmed that the incorporation of the compound according to at least one embodiment of the present disclosure provided excellent light fastness.

In addition, an ink (2) for a resist composition, which had the same composition as that of the ink (1) for a resist composition for a color filter and used the comparative compound (3) instead of the compound (2-10), was stored at normal temperature for 24 hours. As a result, an aggregate was observed in the ink (2) for a resist. Meanwhile, no aggregate or the like occurred in the ink for a resist composition containing the compound according to at least one embodiment of the present disclosure, and hence it was confirmed that the ink was excellent in storage stability.

According to at least one embodiment of the present disclosure, the compound that improves the light fastness of a colored product can be provided. In addition, the liquid composition including the compound, the composition being excellent in storage stability at the time of its storage, can be provided. In addition, according to at least one embodiment of the present disclosure, the thermal transfer recording sheet and the toner each of which provides a recorded product excellent in light fastness can be provided. In addition, according to at least one embodiment of the present disclosure, the resist composition for a color filter that provides a color filter excellent in light fastness can be provided. Further, the color filter excellent in light fastness can be provided.

The compound according to at least one embodiment of the present disclosure is characterized by improving the light fastness of a colored product. In addition, the liquid composition including the compound according to at least one embodiment of the present disclosure is excellent in storage stability. The compound according to at least one embodiment of the present disclosure may be suitably used for improving the light fastness of the colorant of each of a thermal transfer recording sheet, a toner, and a resist composition for a color filter each of which is excellent in light fastness.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A liquid composition comprising:
   a medium; and
   a compound and a coloring material present under one of a dissolved state in the medium and a dispersed state therein,
   wherein the coloring material is a dye selected from the group consisting of a methine-based dye, an azomethine-based dye, and a triphenylmethane-based dye, and
   wherein the compound is represented by formula (1) or (2):

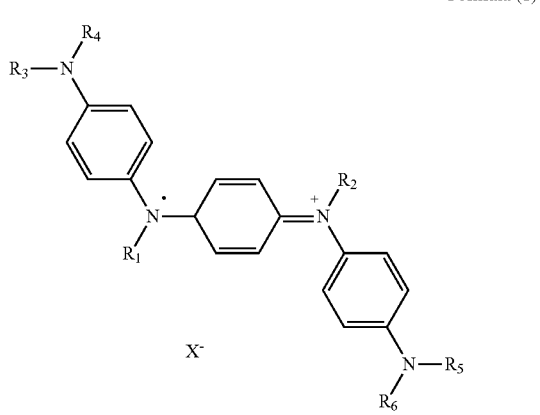

Formula (1)

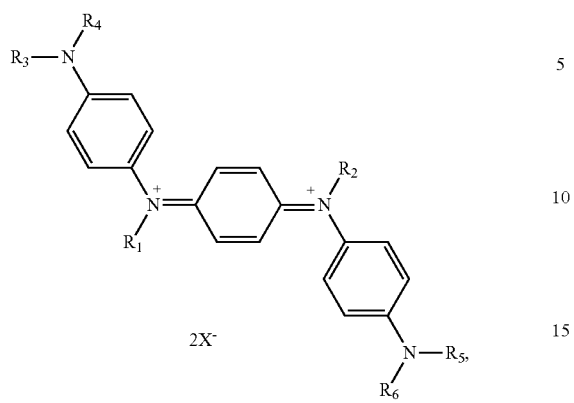

Formula (2)

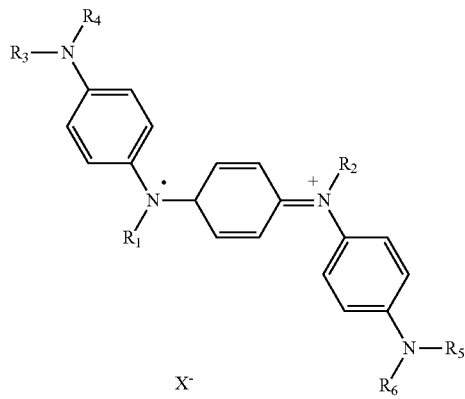

(1)

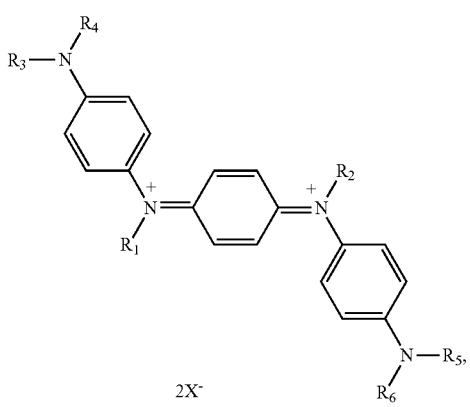

(2)

wherein, in the formula (1) and the formula (2):

$R_1$ and $R_2$ each independently represents an unsubstituted alkyl group having 1 to 8 carbon atoms;

$R_3$ and $R_4$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_3$ and $R_4$ are bonded to each other to form a nitrogen-containing heterocycle;

$R_5$ and $R_6$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_5$ and $R_6$ are bonded to each other to form a nitrogen-containing heterocycle;

a substituent in the substituted alkyl group in any one of $R_3$ to $R_6$ is a cyano group or an alkoxy group, provided that a number of carbon atoms in the substituent is excluded from the number of carbon atoms specified above;

a substituent in each of the substituted alkenyl group, the substituted aralkyl group, and the substituted aryl group each in any one of $R_3$ to $R_6$ is a functional group selected from the group consisting of an alkyl group, a cyano group, and an alkoxy group, provided that a number of carbon atoms in the substituent is excluded from the number of carbon atoms specified above; and $X^-$ represents an anion.

2. A thermal transfer recording sheet comprising:

a substrate; and a coloring material layer formed on the substrate, wherein the coloring material layer contains a compound and a coloring material, wherein the coloring material is a dye selected from the group consisting of a methine-based dye, an azomethine-based dye, and a triphenylmethane-based dye, and wherein the compound is represented by formula (1) or (2):

wherein, in the formula (1) and the formula (2):

$R_1$ and $R_2$ each independently represents an unsubstituted alkyl group having 1 to 8 carbon atoms;

$R_3$ and $R_4$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_3$ and $R_4$ are bonded to each other to form a nitrogen-containing heterocycle;

$R_5$ and $R_6$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_5$ and $R_6$ are bonded to each other to form a nitrogen-containing heterocycle;

a substituent in the substituted alkyl group in any one of $R_3$ to $R_6$ is a cyano group or an alkoxy group, provided that a number of carbon atoms in the substituent is excluded from the number of carbon atoms specified above;

a substituent in each of the substituted alkenyl group, the substituted aralkyl group, and the substituted aryl group each in any one of $R_3$ to $R_6$ is a functional group selected from the group consisting of an alkyl group, a cyano group, and an alkoxy group, provided that a number of carbon atoms in the substituent is excluded from the number of carbon atoms specified above; and $X^-$ represents an anion.

3. A thermal transfer recording sheet comprising:

a substrate; and a coloring material layer and a protective layer formed on the substrate, the coloring material layer and the protective layer being formed field sequentially, wherein the protective layer contains a compound represented by formula (1) or (2):

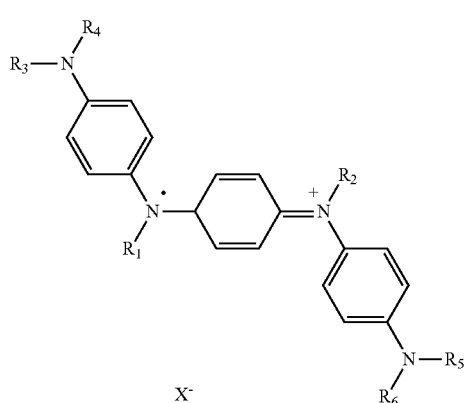

(1)

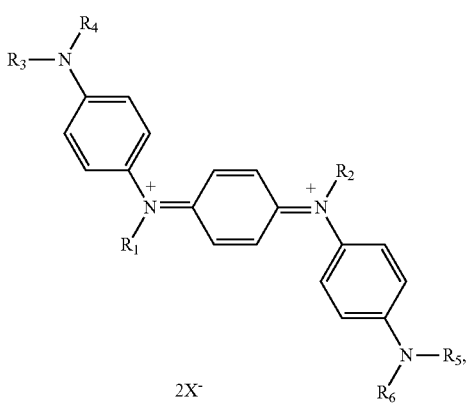

(2)

wherein, in the formula (1) and the formula (2):

$R_1$ and $R_2$ each independently represents an unsubstituted alkyl group having 1 to 8 carbon atoms;

$R_3$ and $R_4$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_3$ and $R_4$ are bonded to each other to form a nitrogen-containing heterocycle;

$R_5$ and $R_6$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_5$ and $R_6$ are bonded to each other to form a nitrogen-containing heterocycle;

a substituent in the substituted alkyl group in any one of $R_3$ to $R_6$ is a cyano group or an alkoxy group, provided that a number of carbon atoms in the substituent is excluded from the number of carbon atoms specified above;

a substituent in each of the substituted alkenyl group, the substituted aralkyl group, and the substituted aryl group each in any one of $R_3$ to $R_6$ is a functional group selected from the group consisting of an alkyl group, a cyano group, and an alkoxy group, provided that a number of carbon atoms in the substituent is excluded from the number of carbon atoms specified above; and $X^-$ represents an anion.

4. The thermal transfer recording sheet according to claim 3, wherein the coloring material layer contains a coloring material, and wherein the coloring material is a dye selected from the group consisting of a methine-based dye, an azomethine-based dye, and a triphenylmethane-based dye.

5. A toner comprising:

a binder resin;

a colorant; and a compound represented by formula (1) or (2):

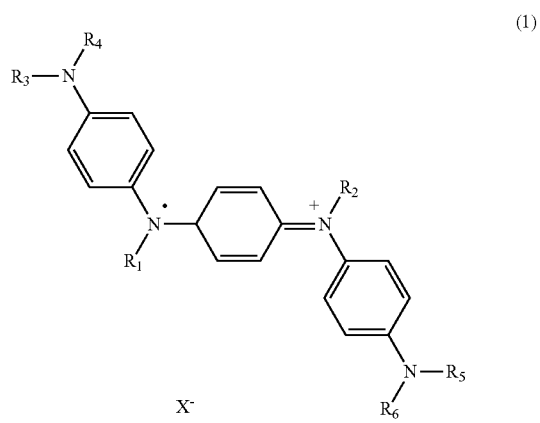

(1)

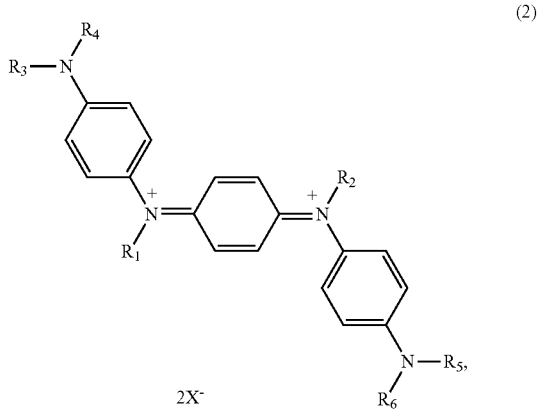

(2)

wherein, in the formula (1) and the formula (2):

$R_1$ and $R_2$ each independently represents an unsubstituted alkyl group having 1 to 8 carbon atoms;

$R_3$ and $R_4$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_3$ and $R_4$ are bonded to each other to form a nitrogen-containing heterocycle;

$R_5$ and $R_6$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_5$ and $R_6$ are bonded to each other to form a nitrogen-containing heterocycle;

a substituent in the substituted alkyl group in any one of $R_3$ to $R_6$ is a cyano group or an alkoxy group, provided that a number of carbon atoms in the substituent is excluded from the number of carbon atoms specified above;

a substituent in each of the substituted alkenyl group, the substituted aralkyl group, and the substituted aryl group each in any one of $R_3$ to $R_6$ is a functional group selected from the group consisting of an alkyl group, a cyano group, and an alkoxy group, provided that a number of carbon atoms in the substituent is excluded from the number of carbon atoms specified above; and $X^-$ represents an anion.

6. The toner according to claim 5, wherein the colorant is a dye selected from the group consisting of a methine-based dye, an azomethine-based dye, and a triphenylmethane-based dye.

7. A resist composition for a color filter comprising:
a binder resin;
a colorant; and
a compound represented by formula (1) or (2):

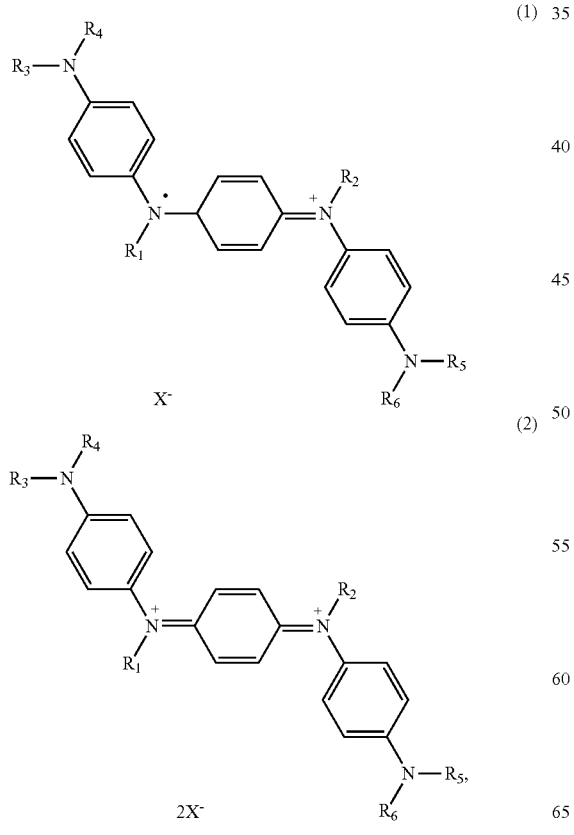

wherein, in the formula (1) and the formula (2):

$R_1$ and $R_2$ each independently represents an unsubstituted alkyl group having 1 to 8 carbon atoms;

$R_3$ and $R_4$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_3$ and $R_4$ are bonded to each other to form a nitrogen-containing heterocycle;

$R_5$ and $R_6$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_5$ and $R_6$ are bonded to each other to form a nitrogen-containing heterocycle;

a substituent in the substituted alkyl group in any one of $R_3$ to $R_6$ is a cyano group or an alkoxy group, provided that a number of carbon atoms in the substituent is excluded from the number of carbon atoms specified above;

a substituent in each of the substituted alkenyl group, the substituted aralkyl group, and the substituted aryl group each in any one of $R_3$ to $R_6$ is a functional group selected from the group consisting of an alkyl group, a cyano group, and an alkoxy group, provided that a number of carbon atoms in the substituent is excluded from the number of carbon atoms specified above; and $X^-$ represents an anion.

8. The resist composition according to claim 7, wherein the colorant is a dye selected from the group consisting of a methine-based dye, an azomethine-based dye, and a triphenylmethane-based dye.

9. A color filter comprising a resist layer containing a compound represented by formula (1) or (2):

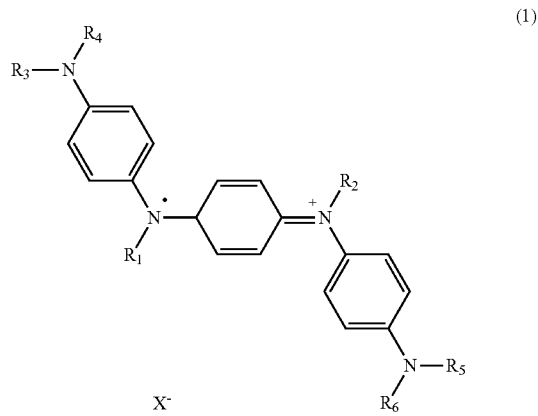

-continued

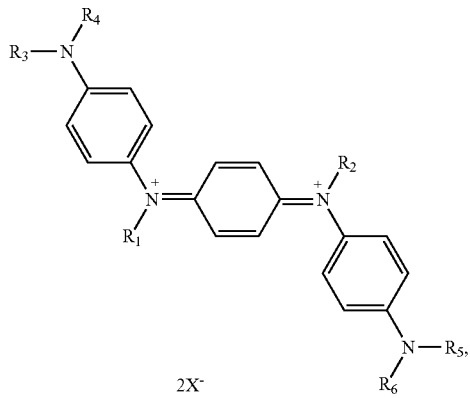

(2)

wherein, in the formula (1) and the formula (2):
$R_1$ and $R_2$ each independently represents an unsubstituted alkyl group having 1 to 8 carbon atoms;
$R_3$ and $R_4$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_3$ and $R_4$ are bonded to each other to form a nitrogen-containing heterocycle;
$R_5$ and $R_6$ each independently represents a hydrogen atom, an unsubstituted alkyl group or substituted alkyl group having 1 to 8 carbon atoms, an unsubstituted alkenyl group or substituted alkenyl group having 2 to 8 carbon atoms, an unsubstituted aralkyl group or substituted aralkyl group having 7 to 12 carbon atoms, or an unsubstituted aryl group or substituted aryl group having 6 to 12 carbon atoms, or $R_5$ and $R_6$ are bonded to each other to form a nitrogen-containing heterocycle;
a substituent in the substituted alkyl group in any one of $R_3$ to $R_6$ is a cyano group or an alkoxy group, provided that a number of carbon atoms in the substituent is excluded from the number of carbon atoms specified above;
a substituent in each of the substituted alkenyl group, the substituted aralkyl group, and the substituted aryl group each in any one of $R_3$ to $R_6$ is a functional group selected from the group consisting of an alkyl group, a cyano group, and an alkoxy group, provided that a number of carbon atoms in the substituent is excluded from the number of carbon atoms specified above; and
$X^-$ represents an anion.

* * * * *